(12) United States Patent
Zeng et al.

(10) Patent No.: US 12,181,404 B2
(45) Date of Patent: Dec. 31, 2024

(54) SYSTEMS AND METHODS FOR DETERMINING PROTEIN CONCENTRATIONS OF UNKNOWN PROTEIN SAMPLES BASED ON AUTOMATED MULTI-WAVELENGTH CALIBRATION

(71) Applicant: AMGEN INC., Thousand Oaks, CA (US)

(72) Inventors: Shang Zeng, Cambridge, MA (US); Gang Xue, Cambridge, MA (US)

(73) Assignee: AMGEN INC., Thousand Oaks, CA (US)

( * ) Notice: Subject to any disclaimer, the term of this patent is extended or adjusted under 35 U.S.C. 154(b) by 362 days.

(21) Appl. No.: 17/632,886

(22) PCT Filed: Aug. 6, 2020

(86) PCT No.: PCT/US2020/045088
§ 371 (c)(1),
(2) Date: Feb. 4, 2022

(87) PCT Pub. No.: WO2021/026284
PCT Pub. Date: Feb. 11, 2021

(65) Prior Publication Data
US 2022/0276157 A1 Sep. 1, 2022

Related U.S. Application Data

(60) Provisional application No. 62/883,320, filed on Aug. 6, 2019.

(51) Int. Cl.
*G01N 21/33* (2006.01)
*G01J 3/28* (2006.01)
*G01N 33/68* (2006.01)

(52) U.S. Cl.
CPC ............ *G01N 21/33* (2013.01); *G01J 3/2823* (2013.01); *G01N 33/6803* (2013.01);
(Continued)

(58) Field of Classification Search
CPC ......... G01J 2003/283; G01J 2003/2833; G01J 3/2823; G01N 21/33; G01N 21/274;
(Continued)

(56) References Cited

U.S. PATENT DOCUMENTS 5,459,677 A   10/1995 Kowalski et al.
2005/0254709 A1*  11/2005 Geshwind ............. G06V 10/56
                                                           382/182

(Continued)

FOREIGN PATENT DOCUMENTS

CN   106769969 A     5/2017
CN   109799203 A  *  5/2019
(Continued)

OTHER PUBLICATIONS

Machine translation of CN-109799203 (Year: 2019).*
(Continued)

*Primary Examiner* — Dani Fox
*Assistant Examiner* — Soorena Kefayati
(74) *Attorney, Agent, or Firm* — MARSHALL, GERSTEIN & BORUN LLP

(57) ABSTRACT ultraviolet (UV) based imaging method for determining protein concentrations of unknown protein samples based on automated multi-wavelength calibration. In various embodiments, a processor receives each of a standard set of wavelength data and an unknown set of wavelength data as recorded by a detector. Each standard set of wavelength data and unknown set of wavelength data defines a series of absorbance-to-wavelength value pairs across a first range of wavelengths selected from a range of a single-wavelength (Continued)

light beams of a UV spectra. The processor generates a multi-wavelength calibration model based on each of a first series of first absorbance-to-wavelength value pairs of the standard set of wavelength data. The processor implements the multi-wavelength calibration model to determine, for each unknown protein sample of the given unknown protein samples, a plurality of protein concentration values.

20 Claims, 10 Drawing Sheets

(52) U.S. Cl.
CPC .............. *G01J 2003/2833* (2013.01); *G01N 2201/127* (2013.01); *G01N 2201/1296* (2013.01)

(58) Field of Classification Search
CPC .. G01N 21/278; G01N 21/276; G01N 21/255; G01N 21/314; G01N 21/05; G01N 2201/129; G01N 2201/1296; G01N 33/6803
See application file for complete search history.

(56) References Cited

U.S. PATENT DOCUMENTS

| | | | |
|---|---|---|---|
| 2006/0097182 A1* | 5/2006 | Itabashi | G01N 33/1806 250/373 |
| 2008/0212071 A1* | 9/2008 | Sterling | A61B 5/14546 356/39 |
| 2010/0253934 A1* | 10/2010 | D'Ascenzi | G01J 3/433 356/326 |
| 2011/0045598 A1 | 2/2011 | Busch et al. | |
| 2012/0327397 A1* | 12/2012 | Tormod | G01N 21/05 356/440 |
| 2013/0143248 A1 | 6/2013 | Fernandez et al. | |
| 2013/0256534 A1* | 10/2013 | Micheels | G01N 21/8507 250/339.07 |
| 2015/0083313 A1* | 3/2015 | Putnam | B32B 38/0004 156/60 |
| 2015/0260656 A1* | 9/2015 | Zilberstein | A61B 5/083 356/402 |
| 2015/0377906 A1 | 12/2015 | Wyrobek et al. | |
| 2017/0029761 A1* | 2/2017 | Hoffmann-Petersen | G01N 21/272 |
| 2017/0176255 A1 | 6/2017 | Neiri | |
| 2019/0057184 A1* | 2/2019 | Pastrana-Rios | G16B 40/10 |
| 2019/0219589 A1* | 7/2019 | Doherty | G06T 7/0012 |
| 2019/0391168 A1* | 12/2019 | Salerno | G01N 21/255 |
| 2021/0024873 A1* | 1/2021 | Yu | C07K 16/00 |
| 2021/0140879 A1* | 5/2021 | Pastrana-Rios | G01N 21/17 |

FOREIGN PATENT DOCUMENTS

| | | |
|---|---|---|
| EP | 1418417 A2 | 5/2004 |
| JP | 2004264279 A | 9/2004 |
| JP | 2012026753 A | 2/2012 |
| WO | WO-93/019364 A1 | 9/1993 |
| WO | WO-2017/174580 A1 | 10/2017 |

OTHER PUBLICATIONS

Busch et al., "Determination of the enantiomeric composition of some molecules of pharmaceutical interest by chemometric analysis of the UV spectra of cyclodextrin guest-host complexes", Analytica Chimica Acta, Elsevier, Amsterdam, NL, vol. 525, No. 1, Nov. 2004, pp. 53-62.
International Search Report and Written Opinion for Application No. PCT/US2020/045088 dated Nov. 19, 2020.
Second Written Opinion for Application No. PCT/US2020/045088 dated May 27, 2021.
International Search Report and Written Opinion for Application No. 11202114560Y, dated May 20, 2024.
Notice of Deficiencies for Israel Patent Application No. 289582, dated Apr. 9, 2024.

* cited by examiner

```
1    #Code Section 1
2    #import code libraries
3    from sklearn.linear_model import LinearRegression
4    import pandas as pd
5
6    #Code Section 2
7    #set default values for standard concentrations
8    standard_concentrations = [0.126, 0.252, 0.504, 1.008, 2.016, 4.032, 8.064,
9    16.128, 32.256, 64.512, 80.64, 100.8, 126]
10
11   #Code Section 3
12   #set default values for linear model R^2 requirement
13   min_score = 0.99
14
15   #Code Section 4
16   #set default values for the range of UV absorbance used for calculation
17   min_abs_std = 0.1
18   max_abs_std = 1.5
19   min_abs_unk = 0.2
20   max_abs_unk = 1.2
21
22   #Code Section 5
23   #read standard set of wavelength data for each standard protein sample of
24   #a set of standard protein samples and assign known concentrations
25   df = pd.read_cvs("standard_sample data.txt")
26   for i in range(1, len(standard_concentrations)):
27       within df, assign known concentrations for each protein standard
28
29   #Code Section 6
30   #data filter for standard with known concentrations
31   def filter_data(x):
32       absorbance = float(x)
33       return - 1 if absorbance < min_abs_std or absorbance > max_abs_std else
34   absorbance
35
36   #Code Section 7
37   #data filter for samples with unknown concentrations
38   def filter_data_unk(x):
39       absorbance = float(x)
40       return - 1 if absorbance < min_abs_unk or absorbance > max_abs_unk else
41   absorbance
42
43
44
45
46
47
```

FIG. 3A

```
48   #Code Section 8
49   #add columns to df and perform Linear Regression
50   for i in range (df):
51           filter x absorbance values using filter_data(x)
52           reg = LinearRegression().fit(x and y values of df)
53           lr_score = reg.score(x and y values of df)
54           if lr_score >= min_score:
55              df.loc[df.index[i], 'coefficient'] = reg.coef_[0]
56              df.loc[df.index[i], 'intercept'] = reg.intercept_
57
58   #Code Section 9
59   #determining protein concentration values of protein samples with
60   unknown concentrations
61   def calc_unk(file_name_of_sample_with_unknown_ concentration):
62
63
64           df_unk = pd.read_cvs(file_name_of_sample_with_unknown_concentration)
65
66       sum = 0.00
67       cnt = 0 for i in range(df_unk):
68              abs = filter x absorbance values using filter_data_unk(x)
69              if abs != -1 and df.loc[df.index[i], 'intercept'] != None:
70
71                  conc = float((abs-df.loc[df.index[i], 'intercept']) /
72                  df.loc[df.index[i], 'coefficient'])
73
74                  print(round(conc,3))
75                  sum = sum + conc
76                  cnt = cnt + 1
77              #avg = sum/cnt
78              #print('the unknown concentration is:' + str(round(avg,2)) + 'mg/ml')
79              return str(round(float(sum/cnt), 3))
80
81   #Code Section 10
82   #Input and Output Screens
83   file_name_of_sample_with_unknown_concentration =
84   input('Please enter your sample name:')
85
86   print('The sample concentration is ' +
87   calc_unk(file_name_of_sample_with_unknown_concnetnratio) + 'mg/ml')
```

FIG. 3B

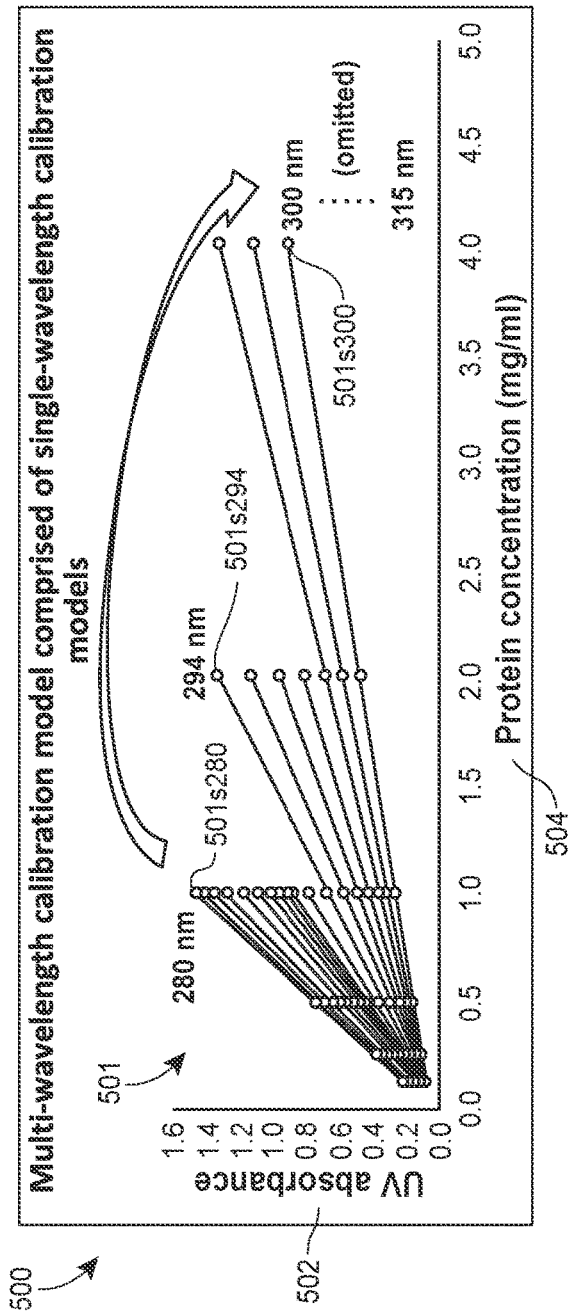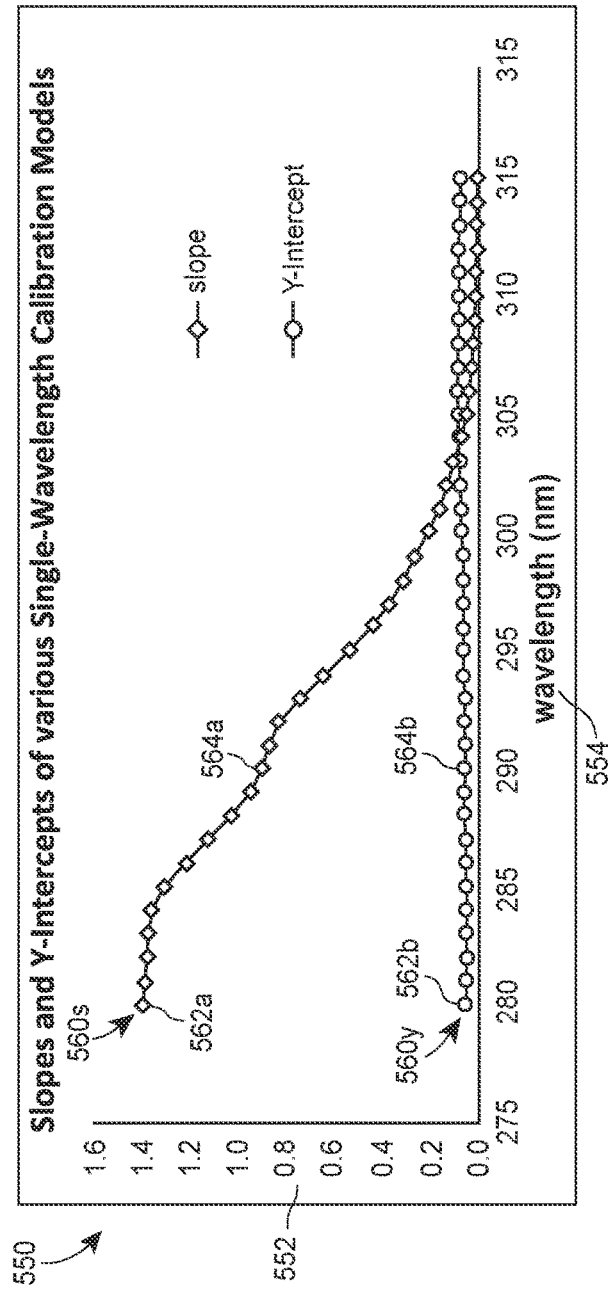
FIG. 5A
FIG. 5B

SYSTEMS AND METHODS FOR DETERMINING PROTEIN CONCENTRATIONS OF UNKNOWN PROTEIN SAMPLES BASED ON AUTOMATED MULTI-WAVELENGTH CALIBRATION

CROSS-REFERENCE TO RELATED APPLICATION

This is the United States national phase of International Patent Application No. PCT/US20/45088, filed Aug. 6, 2020, which claims priority to U.S. Provisional Patent Application No. 62/883,320, filed Aug. 6, 2019, entitled SYSTEMS AND METHODS FOR DETERMINING PROTEIN CONCENTRATIONS OF UNKNOWN PROTEIN SAMPLES BASED ON AUTOMATED MULTI-WAVELENGTH CALIBRATION, the entire contents of each of the foregoing being hereby expressly incorporated by reference herein.

FIELD OF THE DISCLOSURE

The present disclosure generally relates to ultraviolet (UV) based imaging systems and methods related to the automation and engineering of therapeutic pharmaceuticals, and, more particularly, to UV based imaging systems and methods for determining protein concentrations of unknown protein samples based on automated multi-wavelength calibration.

BACKGROUND

Process monitoring and product quality attribute control are routinely performed in the preparation and development of pharmaceutical therapeutic products. For example, techniques regarding process monitoring and product quality attribute control are generally used to ensure the efficacy of such pharmaceutical therapeutic products.

Current instruments, including both current fixed and variable path length instruments (e.g., mechanical instruments), are designed around the application of, and are limited on the dependence of, the Beer-Lambert Law formula, which is linear in nature. In particular, because the linear range of absorbance is limited, such instruments can fail to correctly measure concentration a sample when the absorbance is out of the linear range.

The below formula illustrates the Beer-Lambert Law:

$$A = \varepsilon * C * l$$

In above formula, A is the absorbance value, $\varepsilon$ is the extinction coefficient, C is the concentration value, and l is the path length of the beam of light through the sample. The absorbance value (A) is generally measured as a response factor to the light beam passing through a sample. The extinction coefficient (ε) measures how strong a substance absorbs light at a given wavelength. With respect therapeutics measurement, the extinction coefficient (ε) is generally an inherent property of a protein and does not change.

The concentration value (C) refers to the concentration of a given sample (e.g., sample of a therapeutic or other protein-based product). More generally, concentration is the abundance of a constituent divided by the total volume of a mixture. Concentration may refer to several different types, including mass concentration, molar concentration, number concentration, and/or volume concentration. A concentration may generally be any type of chemical mixture, but most commonly is a solute or solvent solution.

As illustrated above, the Beer-Lambert Law formula assumes linearity such that current protein measurement instruments and techniques are limited to linear functions of a sample concentration value, a fixed extinction coefficient, and the length of a static light path. Application of the Beer-Lambert formula can fail to correctly measure concentration to absorbance rates of a sample that are non-linear which can lead to bias, false positives and/or false negatives during process monitoring and product quality attribute control.

Because of the Beer-Lambert limitations, preparation of samples for measurement and product quality attribute control with fixed-pathlength UV spectrometers is typically both time consuming and error prone. For example, measurement of product quality attributes may require serial dilutions until the sample concentration falls into the dynamic range. Such dilution may easily create errors, especially when measuring values across several product samples, as it may require different dilution factors across samples throughout the process and the usage of dilution factor for concentration calculation can be error-prone. The dilution process applied to several product samples, and errors typically introduced by such process, generally creates differences in the measurements of the related product quality attributes. Such erroneous measurements can lead to an unacceptable number of false positives and false negatives during process monitoring and product quality attribute control.

Variable path length instruments have been developed to allow for the measurement of UV absorbance at variable path length (as opposed to the traditional fixed path length UV absorbance measurement). In such instruments, the pathlength is defined by the distance between the tip of the light delivering Fibrette and the inside bottom of the sample vessel. The pathlength is dynamically controlled, through movement of the Fibrette up and down in the sample, by integrated hardware means. Variable pathlength instruments address the issues of concentration range of direct measurement. In fixed-pathlength instruments, the direct measurement range is narrow, therefore, in practice sample dilution is always required. With variable pathlength instruments, however, since such instruments can scan variable pathlengths, it can directly measure high protein concentration without need of any dilution. Such instruments, however, are typically expensive to acquire and maintain, and, fundamentally, are also prone to measurement error due to the mechanical movement and manipulation of the light delivering Fibrette. For example, lack of routine calibration or maintenance of the Fibrette, and/or slight variations in the mechanics of the variable light instruments, generally results in errors where the results of the measurement are offset by the degree of mechanical failure, mis-calibration, or mechanical variations. These errors generally lead to variance in sample measurement and prevent repeatable results and sufficient calibration within acceptable limits, including, for example, for product measurement and quality control purposes.

For the foregoing reasons, there is a need for UV based imaging systems and methods for determining protein concentrations of unknown protein samples based on automated multi-wavelength calibration.

BRIEF SUMMARY

The present disclosure generally relates to the automation and testing of therapeutic pharmaceuticals, including the development, processing, monitoring, and/or product quality attribute control related to such therapeutic pharmaceuticals. In various embodiments, UV based imaging systems and methods are disclosed for determining protein concentrations of unknown protein samples based on automated multi-wavelength calibration. The determined protein concentrations may be concentrations of unknown samples of therapeutic pharmaceuticals or products. The determination of such protein concentrations may be used in process monitoring and product quality attribute control, for example, during manufacturing of therapeutics, or other protein-based products. The determination of such protein concentrations may also be used in process monitoring and product quality attribute control as related to product quality control and/or to ensure regularity compliance or otherwise efficacy of such products.

Accordingly, as described herein, in various embodiments a UV based imaging system may be configured to determine protein concentrations of unknown protein samples based on automated multi-wavelength calibration. The UV based imaging system may include a light source configured to project a multi-wavelength light beam. In addition, the UV based imaging system may include a monochromator configured to receive the multi-wavelength light beam and to project, based on the multi-wavelength light beam, a range of single-wavelength light beams of a UV spectra.

The UV based imaging system may further include a sample holder operable for receiving a protein sample. In various embodiments, the protein sample may be either of (1) a standard protein sample selected from a set of standard protein samples, or (2) an unknown protein sample selected from a set of unknown protein samples. As described herein, the unknown protein sample has an unknown protein concentration. The sample holder is generally positioned to allow the range of single-wavelength light beams to pass through at least a portion of the protein sample, whether the protein sample is of a standard protein type or an unknown protein type.

The UV based imaging system may further include a detector operable to detect the range of single-wavelength light beams passing through the at least the portion of the protein sample.

The UV based imaging system may further include a memory storing program instructions and a processor communicatively coupled to the memory. The processor may be configured to execute the program instructions to cause the processor to receive a standard set of wavelength data as recorded by the detector for each standard protein sample of the set of standard protein samples. The standard set of wavelength data may include, for each standard protein sample, a first series of first absorbance-to-wavelength value pairs across a first range of wavelengths selected from the range of the single-wavelength light beams. In addition, each first absorbance-to-wavelength value pair may comprise a UV absorbance value and a wavelength value.

In addition, the processor of the UV based imaging system may be further configured to execute the program instructions to cause the processor to generate a multi-wavelength calibration model based on each of the first series of first absorbance-to-wavelength value pairs of the standard set of wavelength data.

The processor of the UV based imaging system may be further configured to execute the program instructions to cause the processor to receive an unknown set of wavelength data as recorded by the detector for each unknown protein sample of the set of unknown protein samples. The unknown set of wavelength data may include, for each unknown protein sample, a second series of second absorbance-to-wavelength value pairs across a second range of wavelengths selected from the range of the single-wavelength light beams. Each second absorbance-to-wavelength value pair may comprise a UV absorbance value and a wavelength value.

In addition, the processor of the UV based imaging system may be further configured to execute the program instructions to cause the processor to determine with the multi-wavelength calibration model, and for each unknown protein sample of the set of unknown protein samples, a plurality of protein concentration values. Each protein concentration value of the plurality of protein concentration values may correspond to the second range of wavelengths selected from the range of the single-wavelength light beams.

In additional embodiments described herein, a UV based imaging method for determining protein concentrations of unknown protein samples based on automated multi-wavelength calibration is described. The UV based imaging method includes receiving, at a processor, a standard set of wavelength data as recorded by a detector for each standard protein sample of a set of standard protein samples. The standard set of wavelength data may include, for each standard protein sample, a first series of first absorbance-to-wavelength value pairs across a first range of wavelengths selected from a range of a single-wavelength light beams of a UV spectra. Each first absorbance-to-wavelength value pair may comprise a UV absorbance value and a wavelength value.

The UV based imaging method may further include generating, with the processor, a multi-wavelength calibration model based on each of the first series of first absorbance-to-wavelength value pairs of the standard set of wavelength data.

The UV based imaging method may further include receiving, at the processor, an unknown set of wavelength data as recorded by the detector for each unknown protein sample of a set of unknown protein samples. The unknown set of wavelength data may include, for each unknown protein sample, a second series of second absorbance-to-wavelength value pairs across a second range of wavelengths selected from the range of the single-wavelength light beams. Each second absorbance-to-wavelength value pair may comprise a UV absorbance value and a wavelength value.

The UV based imaging method may further include determining, with the multi-wavelength calibration model as implemented on the processor, for each unknown protein sample of the set of unknown protein samples, a plurality of protein concentration values. Each protein concentration value of the plurality of protein concentration values may correspond to the second range of wavelengths selected from the range of the single-wavelength light beams.

In additional embodiments described herein, a tangible, non-transitory computer-readable medium storing instructions for determining protein concentrations of unknown protein samples based on automated multi-wavelength calibration is described. The instructions, when executed by one or more processors of a computing device, the computing device including one or more memories, cause the computing device to receive, at a processor, a standard set of wavelength data as recorded by a detector for each standard protein sample of a set of standard protein samples. The standard set of wavelength data may include, for each standard protein sample, a first series of first absorbance-to-wavelength value pairs across a first range of wavelengths selected from a range of a single-wavelength light beams of a UV spectra. Each first absorbance-to-wavelength value pair may comprise a UV absorbance value and a wavelength value.

In addition, the instructions, when executed by the one or more processors may further cause the computing device to generate, with the processor, a multi-wavelength calibration model based on each of the first series of first absorbance-to-wavelength value pairs of the standard set of wavelength data.

Further, the instructions, when executed by the one or more processors, may further cause the computing device to receive, at the processor, an unknown set of wavelength data as recorded by the detector for each unknown protein sample of a set of unknown protein samples. In addition, the unknown set of wavelength data may include, for each unknown protein sample, a second series of second absorbance-to-wavelength value pairs across a second range of wavelengths selected from the range of the single-wavelength light beams. Each second absorbance-to-wavelength value pair may comprise a UV absorbance value and a wavelength value.

In addition, the instructions, when executed by the one or more processors may cause the computing device to determine, with the multi-wavelength calibration model as implemented on the processor, for each unknown protein sample of the set of unknown protein samples, a plurality of protein concentration values. Each protein concentration value of the plurality of protein concentration values may correspond to the second range of wavelengths selected from the range of the single-wavelength light beams.

In additional embodiments described herein, an imaging apparatus for determining protein concentrations of unknown protein samples based on automated multi-wavelength calibration is described. The imaging apparatus includes a means for receiving a standard set of wavelength data for each standard protein sample of a set of standard protein samples. The standard set of wavelength data includes, for each standard protein sample, a first series of first absorbance-to-wavelength value pairs across a first range of wavelengths selected from a range of a single-wavelength light beams of a UV spectra. Each first absorbance-to-wavelength value pair comprises a UV absorbance value and a wavelength value.

The imaging apparatus further includes a means for generating a multi-wavelength calibration model based on each of the first series of first absorbance-to-wavelength value pairs of the standard set of wavelength data.

The imaging apparatus further includes a means for receiving an unknown set of wavelength data for each unknown protein sample of a set of unknown protein samples. The unknown set of wavelength data includes, for each unknown protein sample, a second series of second absorbance-to-wavelength value pairs across a second range of wavelengths selected from the range of the single-wavelength light beams. Each second absorbance-to-wavelength value pair comprises a UV absorbance value and a wavelength value.

The imaging apparatus further includes a means for determining, with the multi-wavelength calibration model, for each unknown protein sample of the set of unknown protein samples, a plurality of protein concentration values. Each protein concentration value of the plurality of protein concentration values corresponds to the second range of wavelengths selected from the range of the single-wavelength light beams.

The UV based imaging systems and methods of the present disclosure improve over the limitations of currently known instruments. For example, as described herein, the UV based imaging systems and methods of the present disclosure describe an automated workflow for process monitoring and product quality attribute control used in the preparation and development of pharmaceutical therapeutic products. In addition, the automated workflow enhances and improves currently known methods by providing a full scan of a UV spectra instead of being limited to a single or dual wavelength. For example, instead of reliance on a single UV wavelength (e.g., 280 nm) to measure sample protein concentration, as is typical in conventional instrumentations, the UV based imaging systems and methods of the present disclosure measures protein concentration allow for scanning over a wide range, including, for example, a UV range of 280-315 nm.

In addition, the UV based imaging systems and methods of the present disclosure overcome limitations on both fixed path length and multipath length UV spectrometers, including conventional problems related to dynamic range of measuring light wavelengths, absorbance values, and mechanical challenges introduced by more recent instruments. For example, current instruments rely on, and are limited by, application of the Beer-Lambert Law. To overcome the linearity limitation of Beer-Lambert Law, the UV based imaging systems and methods of the present disclosure are configured to detect absorbance values for each wavelength measured for a given sample, and then dynamically calibrate the absorbance response factor according to the change in a related extinction coefficient. As a result, a fixed-path length UV spectrometer, and its related data output, may be improved applying the UV based imaging systems and methods of the present disclosure, which would provide accurate measurement of protein concentrations over a wide range, including, for example, over the range of 0.1-126 milligrams (mg) per milliliter (mL).

In addition, in various embodiments, the UV based imaging systems and methods of the present disclosure generally produce overlaps in wavelength values over the wide ranges of protein concentration measurements. In such embodiments, an enhanced prediction (e.g., an enhanced precision of concentration measurement) may be generated by applying an average, median, derivation, derivative, or otherwise compiling, the range of wavelengths to produce an enhanced, multi-sample measure. For example, in some embodiments, a signal average may be applied to an overlapped concentration measurement, resulting in the enhanced precision. For example, the "enhanced" prediction may have greater accuracy (such as a tighter confidence interval or smaller standard error) relative to a reference prediction based on a single wavelength.

Moreover, unlike variable UV path length instruments that use the mechanical light guides to scan at different path lengths, and thereby extend the linear protein concentration range, the native extinction coefficient tuning of the present UV based imaging systems and methods carries no mechanical error and is applicable with any conventional UV spectrometer.

In addition, the UV based imaging systems and methods of the present disclosure provide improvements in computer functionality and/or in improvements to other technologies at least because the UV based imaging systems and methods improve the accuracy and precision of computing devices, such as spectrophotometers, that measure information of protein-related products. That is, the present disclosure describes improvements in the functioning of a computer device itself (e.g., a spectrophotometer or a device or system used in the measurement or monitoring of protein related products) because application of the UV based imaging techniques described herein increases accuracy and precision of such instruments, devices, or systems, which leads to increased reliability in not only the underlying system, but also the end use of the system, e.g., monitoring and/or measuring of protein concentrations of protein-related product such as therapeutics, as described herein. This improves over the prior art at least because existing instruments, such as fixed-path length instruments and mechanical, variable based instruments are limited, error prone, and or expensive to employ as described herein. In contrast, the UV based imaging systems and methods of the present disclosure is compatible with any full scan capable UV spectrometer. This allows for deployment of the UV based imaging systems and methods throughout an analytical monitoring and/or testing network. For similar reasons, the disclosed systems and methods expand the analytical capability of existing systems and instruments without need for capital investment or a large equipment footprint.

Similarly, the UV based imaging systems and methods of the present disclosure relates to improvement to other technologies or technical fields in the field of automation and engineering of therapeutic pharmaceuticals at least because the UV based imaging systems and methods provide a fully automated workflow enabling real-time measurement and monitory with zero offline sample and data handling. With such automated workflow, sample dilution and manual data processing may be eliminated or decreased, which, decreases human error and increases reliability of the overall process.

As described herein, at least in some embodiments, the UV based imaging systems and methods includes use and application of, or by use of, a particular machine, e.g., a spectrophotometer and/or related components used in by spectrophotometers or other such UV imaging devices.

In addition, the UV based imaging systems and methods of the present disclosure includes effecting a transformation or reduction of a particular article to a different state or thing, e.g., the transformation or reduction of a multi-wavelength light beam into a multi-wavelength calibration model for predicting plurality of protein concentration values that may be used to monitor or measure protein concentration of a protein-related product. Such monitoring and measuring may be used during manufacture of the protein-related product and/or may be used to determine whether the protein-related product is compliant with known specifications or regulations associated with the protein-related product, e.g., for therapeutic products or the manufacture thereof. By way of example, based on the measured protein concentration, the protein concentration of the protein-related product may be increased or decreased to fall within a specified range of protein concentration. By way of example, a batch of protein-related product may be accepted or rejected depending on whether the measured protein concentration falls within or outside of (respectively) a specified range.

In addition, the UV based imaging systems and methods of the present disclosure includes specific features other than what is well-understood, routine, conventional activity in the field, or adding unconventional steps that confine the claim to a particular useful application, e.g., including the application of predictions, enhancements, and measurements that current instruments lack. For example, conventional instruments are limited by dependence on Beer-Lambert Law, mechanical instruments (e.g., guide lights) or manipulation, etc. as described herein, which the UV based imaging systems and methods of the present disclosure overcome.

Advantages will become more apparent to those of ordinary skill in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the system and methods disclosed therein. It should be understood that each Figure depicts an embodiment of a particular aspect of the disclosed system and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and instrumentalities shown, wherein:

FIGS. 3A and 3B illustrate an example computer program listing including pseudo code for implementing the UV based imaging method of FIGS. 2A and 2B in accordance with various embodiments disclosed herein.

FIG. 5A illustrates a diagram representing a multi-wavelength calibration model comprised of single-wavelength calibration models, in accordance with various embodiments disclosed herein.

FIG. 5B illustrates a diagram representing slopes and y-intercepts of the various single-wavelength calibration models of FIG. 5A, in accordance with various embodiments disclosed herein.

The Figures depict preferred embodiments for purposes of illustration only. Alternative embodiments of the systems and methods illustrated herein may be employed without departing from the principles of the invention described herein.

DETAILED DESCRIPTION

Figure 1:
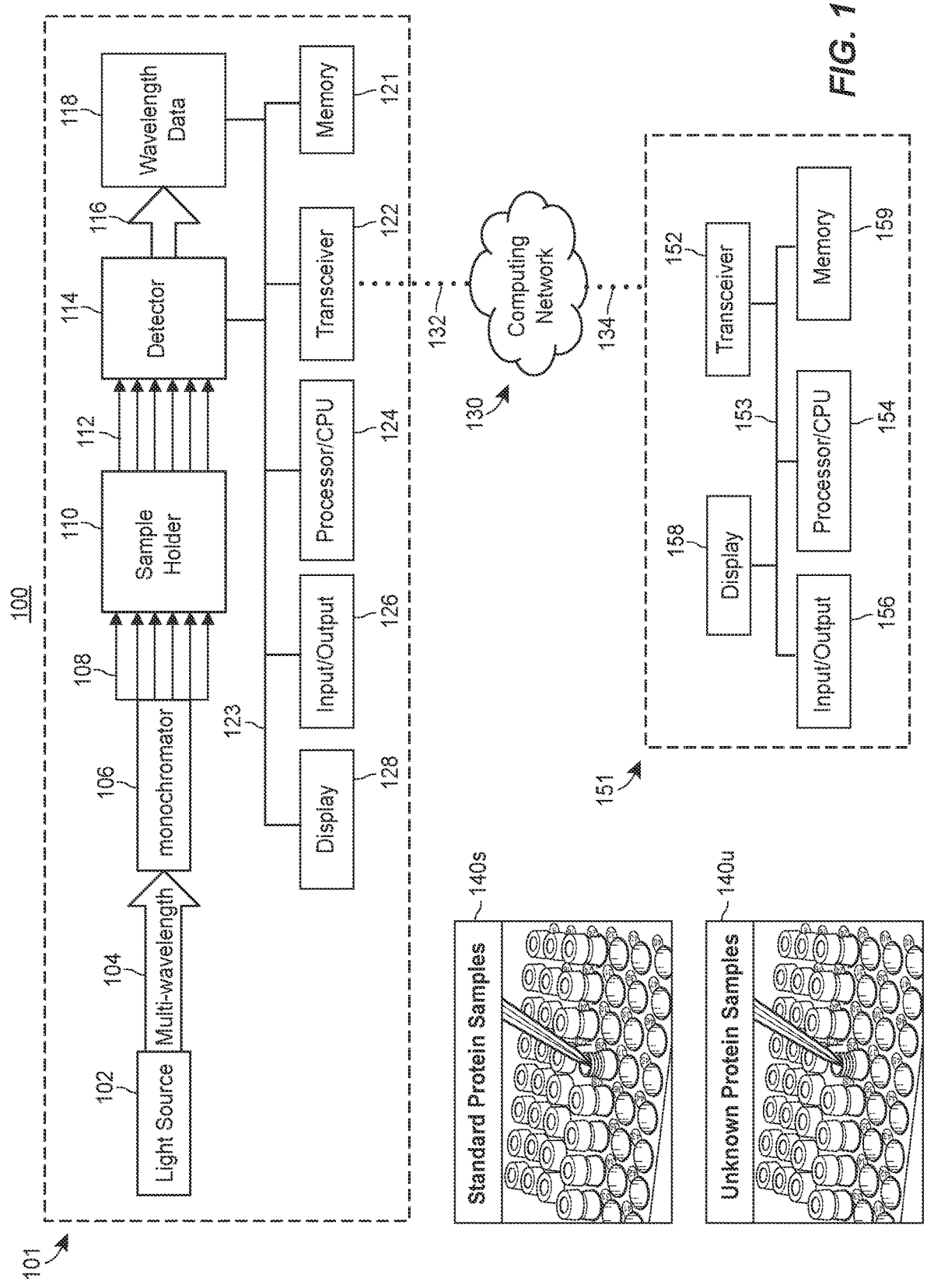
FIG. 1 illustrates an example UV based imaging system for determining protein concentrations of unknown protein samples based on automated multi-wavelength calibration in accordance with various embodiments disclosed herein.

FIG. 1 illustrates an example UV based imaging system 100 for determining protein concentrations of unknown protein samples based on automated multi-wavelength calibration, in accordance with various embodiments disclosed herein. In various embodiments, system 100 may comprise a UV imaging device 101, which can be UV spectrophotometer or other such imaging apparatus. UV imaging device 101 includes light source 102 configured to project a multi-wavelength light beam 104 onto monochromator 106. In various embodiments, monochromator 106 may be a prism, a diffracting device, or any other device implementing diffraction grating to split the multi-wavelength light beam into single-wavelength light beams. In the embodiment of FIG. 1, monochromator 106 is configured to receive multi-wavelength light beam 104, and to project or otherwise provide, using multi-wavelength light beam 014 as a source, a range of single-wavelength light beams 108 of a UV spectra.

In various embodiments, the range of single-wavelength light beams 108 may comprise single-wavelength light beams in the UV spectra from 200 nanometers (nm) to 400 nanometers (nm). In addition, the single-wavelength light beams 108 may include a high number of wavelengths (e.g., a multiple of wavelengths spread over small spans the UV spectra) where each interval of a single-wavelength light beam 108 is a wavelength in the UV spectra. For example, in some embodiments, each single-wavelength light beam 108 in the UV spectra may be separated by a single nanometer interval. Different intervals and interval sizes, however, are contemplated herein such that a single nanometer interval serves as but one example embodiment.

UV imaging device 101 may further include a sample holder 110 operable to receive, hold, or position a protein sample with respect to UV imaging device 101. Sample holder 110 may be configured to hold at least a portion of, a flow through cell, a cuvette, or, other container for encapsulating the protein sample. Sample holder 110 is generally positioned within, or as part of, UV imaging device 101, to allow the range of single-wavelength light beams to pass through at least a portion of the protein sample, whether the protein sample is of a standard protein type or an unknown protein type. The sample holder may be formed of plastic, glass, fused quartz, or other such material that allows the transmission of light to pass through the material and the protein sample.

In various embodiments, the protein sample may be either a standard protein sample (e.g., standard protein samples 140s) or an unknown protein sample (e.g., unknown protein samples 140u) in accordance with various embodiments herein. The term "unknown protein sample" as used herein refers to a protein sample having an unknown protein concentration. Protein samples may be in liquid, semi-liquid, solid, or other states for measurement. The protein of a given protein sample may be a proprietary protein of a therapeutic pharmaceutical product.

As described in various embodiments herein, the unknown protein sample has an unknown protein concentration and the standard protein sample has a known protein concentration. Note that unknown protein samples comprise at least one protein of an unknown concentration; of course, more than one protein can be present. The sample may comprise other non-protein containing components, such as buffers, salts, and other organic and inorganic molecules. The standard protein sample may be a reference standard or other known, pre-measured, or predetermined sample having a known, pre-measured, or predetermined dilution, concentration, or other known protein-based percentage or apportionment.

In various embodiments, the protein sample may be either of (1) a standard protein sample selected from a set of standard protein samples (e.g., standard protein samples 140s), or (2) an unknown protein sample selected from a set of unknown protein samples (e.g., unknown protein samples 140u). As used herein, a set of protein samples (e.g., standard or unknown) comprises one or many protein samples. For example, in one embodiment a set of standard protein samples (e.g., standard protein samples 140s) may comprise a plurality of standard protein samples (e.g., standard protein samples 140s) having respective known concentrations and a set of unknown protein samples (e.g., unknown protein samples 140u) may comprise a single protein sample having an unknown protein concentration.

UV imaging device 101 may further include detector 114 operable to detect a range of single-wavelength light beams 112 passing through the at least a portion of the protein sample, as maintained by sample holder 110. Single-wavelength light beams 112 may comprise a same or a different number, type, strength, and/or magnitude of light as single-wavelength light beams 108. The similarity or differences between single-wavelength light beams 108 and multi-wavelength light beams 112 are generally caused by the protein sample (and its related protein concentration) positioned within sample holder 110, where such similarity or differences cause the generation and/or output 116 of wavelength data 118 (e.g., for either standard or unknown samples) specific to that protein sample (as based on its protein concentration) as recorded by detector 114.

Detector 114 may be, or my comprise, a photomultiplier tube, a photodiode, a photodiode array, a charge-coupled device (CCD), or other light-sensitive device or array configured to collect, and/or record respective values for, light of various wavelengths. For example, for a CCD-based detector, single-wavelength light beams 112 may be focused onto a pixel array of detector 114 where an intensity of each wavelength (e.g., each color if in the visible region) may be measured, and recorded as value(s), by a pixel of the array. The CCD-based detector may then output 116 its measured values, as wavelength data 118, which may together represent a spectrum or values(s) of intensity of each wavelength of light. More generally, wavelength data 118 measures an absorbance value of the protein sample being measured (e.g., the absorbance of the protein concentration of the protein sample currently in sample holder 110). That is, at least some of the single-wavelength light beams 108 passing through sample holder 110 are at least partially absorbed or are otherwise varied according to a protein sample's concentration such that the single-wavelength light beams 112 are also similarly varied. For example, if a protein sample positioned in sample holder 110 absorbed a certain wavelength of light, then that wavelength of light would be absent or partially absent in single-wavelength light beams 112. Accordingly, in general, detector 114 measures variance between the single-wavelength light beams 108 and single-wavelength light beams 112 to determine absorbance, or absorbance values, as response factor(s).

At least in some embodiments, each of light source 102, monochromator 106, sample holder 110, and detector 118 of UV imaging device 101 may form at least a portion of a spectrophotometer device. For example, at least in one embodiment, the spectrophotometer may be a THERMO FISHER SCIENTIFIC™ EVOLUTION™ spectrophotometer or other such imaging apparatus.

Detector 114 may be communicatively coupled via bus 123 (i.e., an electronic communications bus) to various components 121 to 128 of UV imaging device 101. For example, detector 114 may be communicatively coupled to processor 124. Processor 124 may be a microprocessor, or central processing unit (CPU) such as an INTEL®-based, AMD®-based, or other such microprocessor. Processor 124 may be responsible for the control of the various components communicatively coupled via bus 123. For example, processor 124 may control output 116 of detector 114 as wavelength data 118, which, in one embodiment, is stored in memory 121. In addition, processor 124 may receive commands or other instructions from input/output component 126. Input/output component 126 may be interfaced with, or otherwise connected to, various input/output devices, such as keyboard, mouse, or similar components. Such components may be used to access or otherwise manipulate or retrieve wavelength data 118 (e.g., in memory 121) as output 116 detector 116. Processor 124 may also be communicatively connected to display 128. Display 128 may be a display screen, where processor 124 would render a representation, such as a two-dimensional (2D), three-dimensional (3D), or other representation of wavelength data 118 on the display screen of display 128.

Processor 124 may further be communicatively connected, via bus 123, to transceiver 122. Processor 124, via transceiver 122, may be communicatively coupled over computing network 130 to computing device 151. In the displayed embodiment, computing device 151 may send 134 and receive 132 data (e.g., such as wavelength data 118) via computer network 130, via a remote processor 154 and remote transceiver 152 of computing device 151. Remote processor 154 and remote transceiver 152 may be communicatively coupled to one another via bus 153 (e.g., an electronic communications bus). Computing device 151 may further include remote memory 159, communicatively coupled via bus 153, to store data (e.g., wavelength data 118) as received via remote transceiver 152. Computing device 151 may further include display 158 and input/output component 156, communicatively coupled via bus 153, to facilitate input/output operations, e.g., such as receiving commands via touchscreens, keyboards, etc. and display data, e.g., wavelength data 118, on a screen of display 158. In this way, computing device 151 includes a remote processor 154 and a remote memory 159 that may be used to store and/or process wavelength data 110 remotely from UV imaging device 101.

Figure 2A:
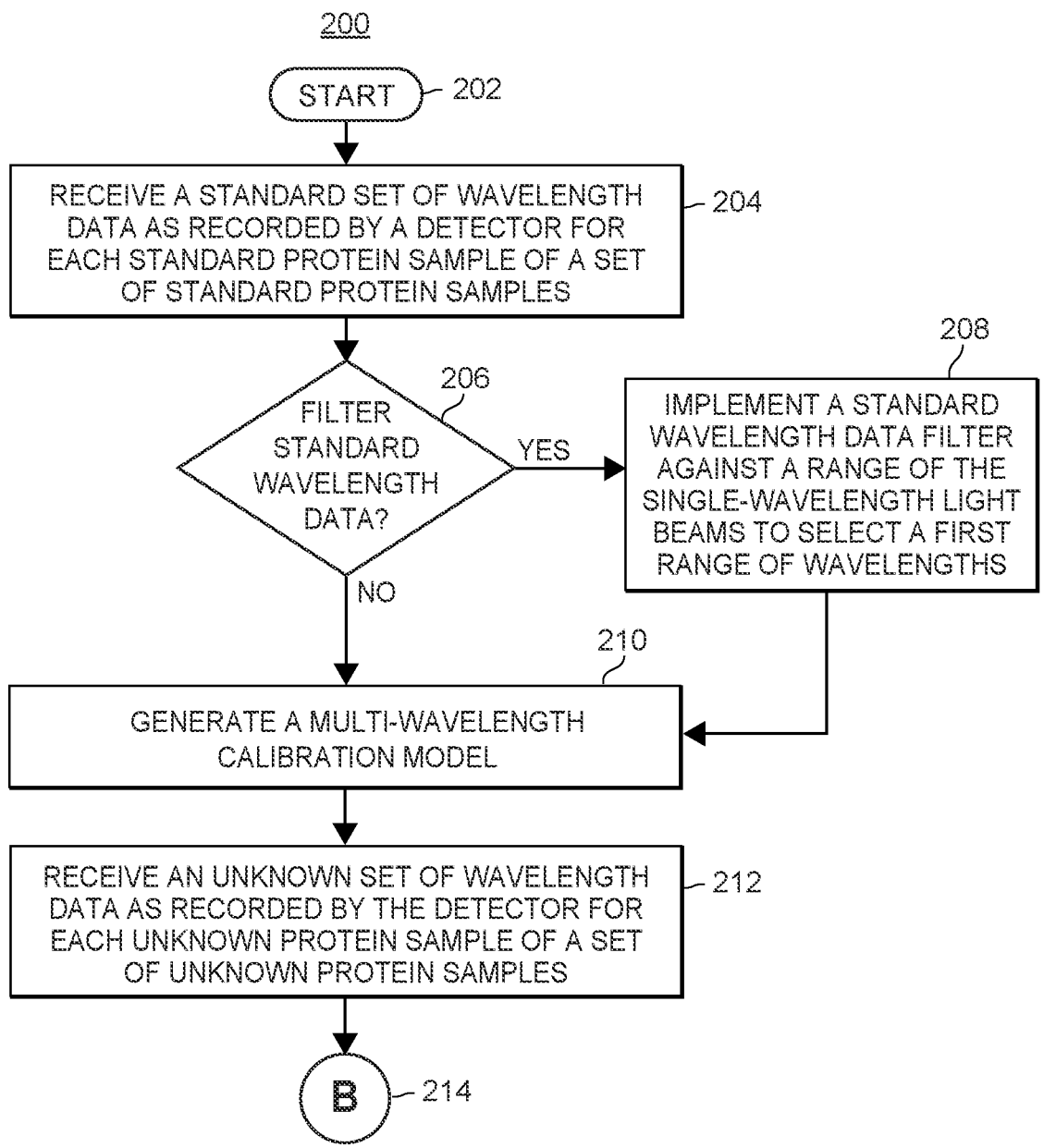
FIGS. 2A and 2B illustrate a flow diagram of an example UV based imaging method for determining protein concentrations of unknown protein samples based on automated multi-wavelength calibration in accordance with various embodiments disclosed herein.
Figure 2B:
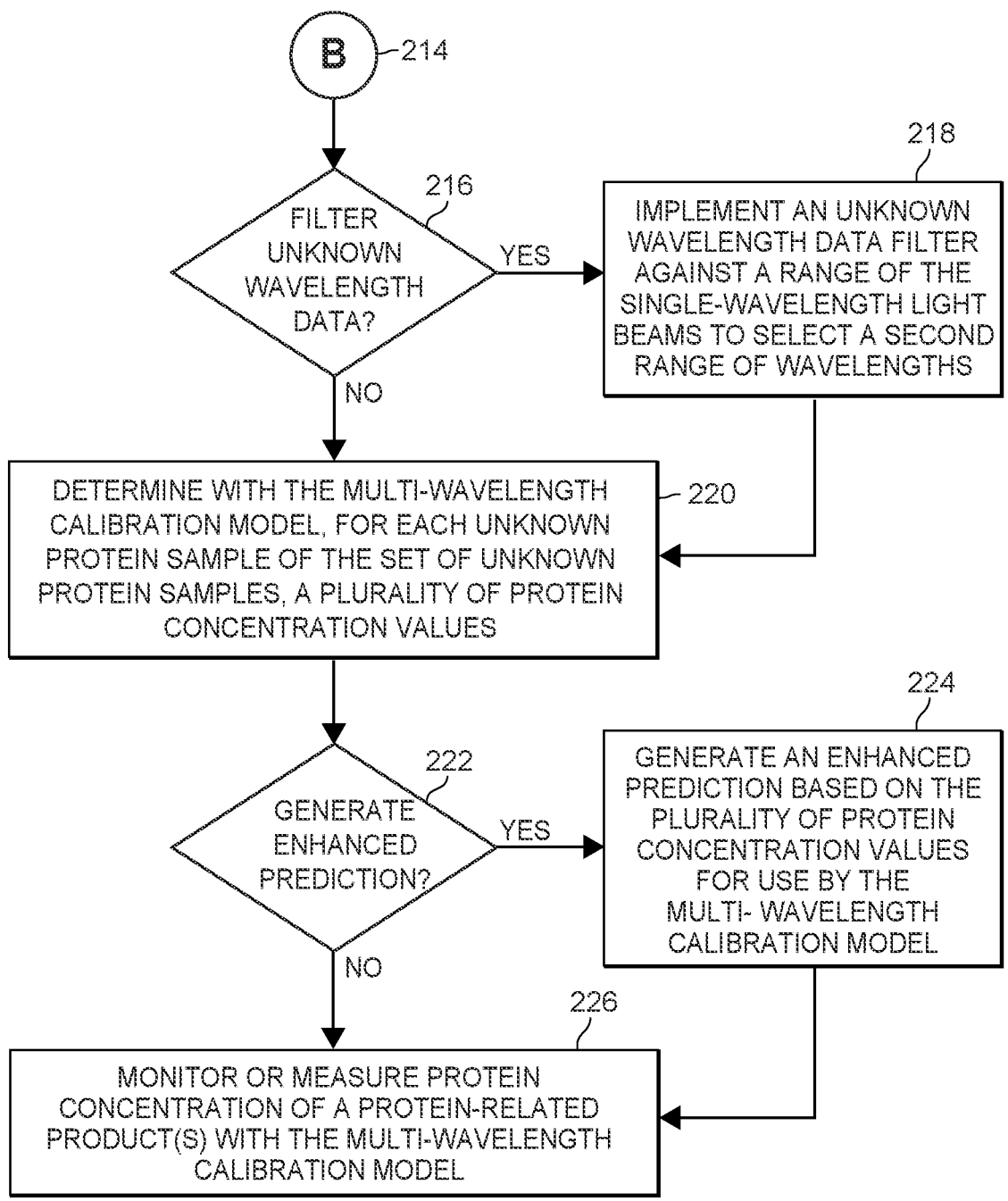

In the embodiment of FIG. 1, memory 121 and/or remote memory 159 may store program instructions to cause either one or both of processors 124 and/or 154 to execute the program instructions to implement UV based imaging method 200 as described by FIGS. 2A and 2B herein. The program instructions may be program code in a programming language such as Python, Java, C #, or other programming language. In some embodiments, the program instructions may be client-server based, where remote processor 154 communicates as a client to processor 124 as a server over computing network 130. In such embodiments, remote processor 154 may request data, such as wavelength data 118 (e.g., as stored in memory 121 or as newly output 116 by detector 114) to be transmitted from UV imaging device 101 to computing device 151. The wavelength data 118 may be requested by remote processor 154 via an online application programming interface (API) such as representational state transfer (RESTful) API, where processor 124 implements the API to receive requests from remote processor 154 and responds by providing wavelength data 118 via computer network 130. In other embodiments, UV imaging device 101 may implement a push-based interface, where newly generated and/or output 116 wavelength data 118 is transmitted via computer network 130 to computing device 151. In still further embodiments, a user of either UV imaging device 101 or computing device 151 may, via input/output 126 or 156, receive or extract wavelength data on an external storage device (not shown), such as a disk or thumb drive.

FIGS. 2A and 2B illustrate a flow diagram of an example UV based imaging method 200 for determining protein concentrations of unknown protein samples (e.g., unknown protein samples 140$u$) based on automated multi-wavelength calibration in accordance with various embodiments disclosed herein. UV based imaging method 200 overcomes limitations of the prior art, including reliance on the Beer-Lambert Law and its assumptions and limitations regarding linearity. FIGS. 2A and 2B are shown in conjunction with FIGS. 3A and 3B. FIGS. 3A and 3B illustrate an example computer program listing including pseudo code for implementing the UV based imaging method 200 of FIGS. 2A and 2B in accordance with various embodiments disclosed herein. As shown with respect to FIGS. 3A and 3B, to overcome the linearity limitations of the Beer-Lambert Law, a program code (as illustrated in pseudo-Python code) may apply sample filters to determine linear absorbance ranges of each wavelength and dynamically calibrate absorbance response factors according to change(s) in extinction coefficient(s). As a result, UV imaging device 101 (e.g., including embodiments where UV imaging device 101 is a fixed-path length UV spectrometer) may accurately measure protein concentration(s) over a wide range, e.g., protein concentrations within a range of 0.1 to 126 mg/mL.

As depicted by FIG. 2A, UV based imaging method 200 begins (202) at block 204 where a processor (e.g., processor 125 or remote processor 154) receives a standard set of wavelength data (e.g., wavelength data 118) as recorded by a detector (e.g., detector 114) for each standard protein sample of a set of standard protein samples (e.g., standard protein samples 140$s$). In some embodiments, for example, the standard set of wavelength data (e.g., wavelength data 118) may be received as comma separated value (CSV) data. In other embodiments, the standard set of wavelength data may be received in a database format, extensible markup language (XML), JavaScript Object Notation (JSON), or other data or textual format. In the embodiment computer program listing of FIGS. 3A and 3B, for example, at Code Section 5, wavelength data of standard protein samples (e.g., standard protein samples 140$s$) is read into memory (e.g., memory 121 or remote memory 159) by a processor (e.g., processor 124 or remote processor 154) as CSV data, where each protein standard sample is assigned its known concentration. Computer program listing of FIGS. 3A and 3B is prepared in a pseudo-Python, where the pandas library as "pd" is used to read in the wavelength data. This is shown in Code Sections 1 and 5. Code Section 1 also shows the importation of additional library "sklearn," which provides a linear regression training algorithm as an embodiment used to illustrated the training of predictive models as described herein.

Figure 4A:
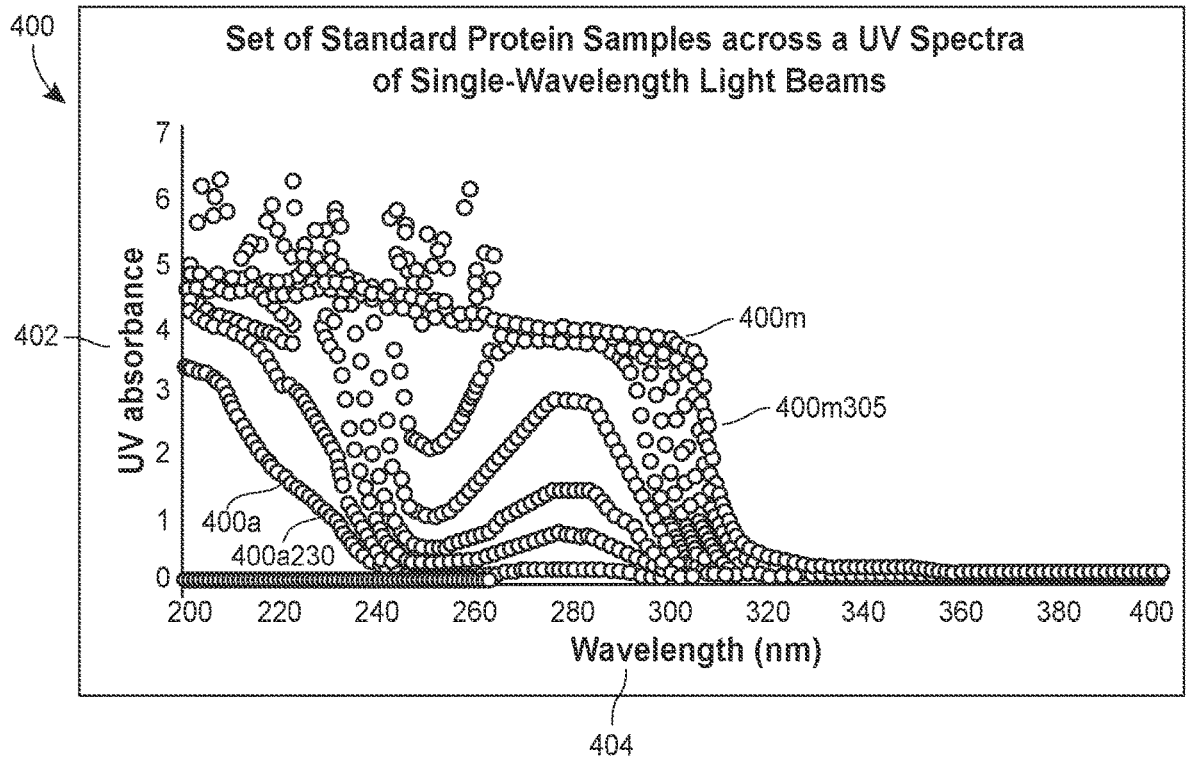
FIG. 4A illustrates a diagram representing a set of standard protein samples across a UV spectra of single-wavelength light beams, in accordance with various embodiments disclosed herein.

The standard set of wavelength data (e.g., wavelength data 118) may include, for each standard protein sample, a first series of first absorbance-to-wavelength value pairs across a first range of wavelengths selected from a range of a single-wavelength light beams of a UV spectra. Each first absorbance-to-wavelength value pair may comprise a UV absorbance value and a wavelength value. For example, FIG. 4A illustrates a diagram 400 representing a set of standard protein samples (e.g., standard protein samples 140s) 400a to 400m across a UV spectra of single-wavelength light beams 404, in accordance with various embodiments disclosed herein. In particular, diagram 400 includes a UV absorbance axis 402 (y-axis) with a range of absorbance values, which are used as a response factor measurement. Generally, the larger the absorbance value, the less light was detected (e.g., by detector 114) for a given wavelength. In addition, diagram 400 includes a wavelength axis 404 (x-axis) with a range of light wavelengths in intervals of nanometers, although other intervals are contemplated herein.

In the embodiment of FIG. 4A, standard protein samples (e.g., standard protein samples 140s), having protein standard solutions in the range of 0.1-126 mg/ml, were scanned via a spectrophotometer over the 200-400 nm UV spectra (with 1 nm interval). The standard protein samples were contained in a 1 cm-path length quartz cuvette. The wavelength data of the UV spectra was saved as CSV data. Accordingly, diagram 400 depicts the raw UV spectra data of protein calibration standards (e.g., standard protein samples (e.g., standard protein samples 140s)) scanned in wavelength range of 200 nm to 400 nm.

As shown in FIG. 4A, diagram 400 represents 13 standard protein samples (e.g., standard protein samples 140s) 400a to 400m. For each standard protein sample, a same protein (e.g., a protein molecule) is measured by protein concentration. The protein molecule may be a molecule, such as a proprietary protein or other protein used to develop therapeutic products or other such pharmaceutical products.

As shown in FIG. 4A, each standard protein sample (e.g., standard protein sample 400a and standard protein sample 400m) is represented by a corresponding plot of multiple absorbance-to-wavelength value pairs within diagram 400. With respect to standard protein sample 400m, for example, absorbance-to-wavelength value pair 400m305 is a measurement of standard protein sample 400m at wavelength value of 305 having an absorbance value of approximately 2.5. Accordingly, absorbance-to-wavelength value pair 400m305 is positioned within diagram 400 at the corresponding UV absorbance axis 402 (y-axis) and the corresponding wavelength axis 404 (x-axis). As a further example, respect to standard protein sample 400a, absorbance-to-wavelength value pair 400a230 is a measurement of standard protein sample 400a at wavelength value of 230 and having an absorbance value of approximately 1.0. Accordingly, absorbance-to-wavelength value pair 400a230 is positioned within diagram 400 at the corresponding UV absorbance axis 402 (y-axis) and the corresponding wavelength axis 404 (x-axis). The remaining absorbance-to-wavelength value pairs of respective standard protein sample representations 400a to 400m are similarly plotted within diagram 400 each representing UV absorbance values (along UV absorbance axis 402) scanned and measured at each wavelength value (along wavelength axis 404) in the wavelength spectra from 200 nanometers (nm) to 400 nanometers (nm).

With respect to UV based imaging method 200 of FIG. 2A, at block 206 the processor (e.g., processor 124 or remote processor 154) determines whether to filter the standard set of wavelength data. The determination may be made based on the range of the wavelength data detected (e.g., by detector 114), where some datasets include wide wavelength ranges. If no filter is applied, UV based imaging method 200 proceeds to block 210.

At block 208, however, a standard wavelength data filter is applied. The standard wavelength data filter may comprise a set of program instructions stored in a memory of UV imaging system 100, for example, in memory 121 or remote memory 154. In the computer program listing of FIGS. 3A and 3B, for example, pseudo-Python instructions illustrate an embodiment a standard wavelength data filter (Code Section 6) for removing data points out of the original single-wavelength light range and original UV absorbance value range of FIG. 4A to ensure an optimal data quality used to train calibration models as described herein. In the example of FIG. 3A, Code Section 6 applies filtering criteria, set as user-defined variables (Code Section 4), to allow flexible manipulation of the filtered ranges. For example, as shown in Code Section 4, filtering criteria of standard protein samples (e.g., standard protein samples 140s) is configured to select data points with a UV absorbance of 0.1 to 1.5 for the wavelength range of 280 to 315 nm.

At block 208, a processor (e.g., processor 124 or remote processor 154) implements the standard wavelength data filter against a range of the single-wavelength light beams to select or limit a first range of wavelengths. In addition, the processor may implement the standard wavelength data filter to select or limit each first series of first absorbance-to-wavelength value pairs based on UV absorbance values within a first filter range of UV absorbance values. For example, application of the standard wavelength data filter (e.g., at block 208) yields diagram 450 of FIG. 4B which represents a limited or filtered set of data ranges (in both wavelength and absorbance values, i.e., absorbance-to-wavelength value pairs) of the plotted absorbance-to-wavelength value pairs of diagram 400 of FIG. 4A.

Figure 4B:
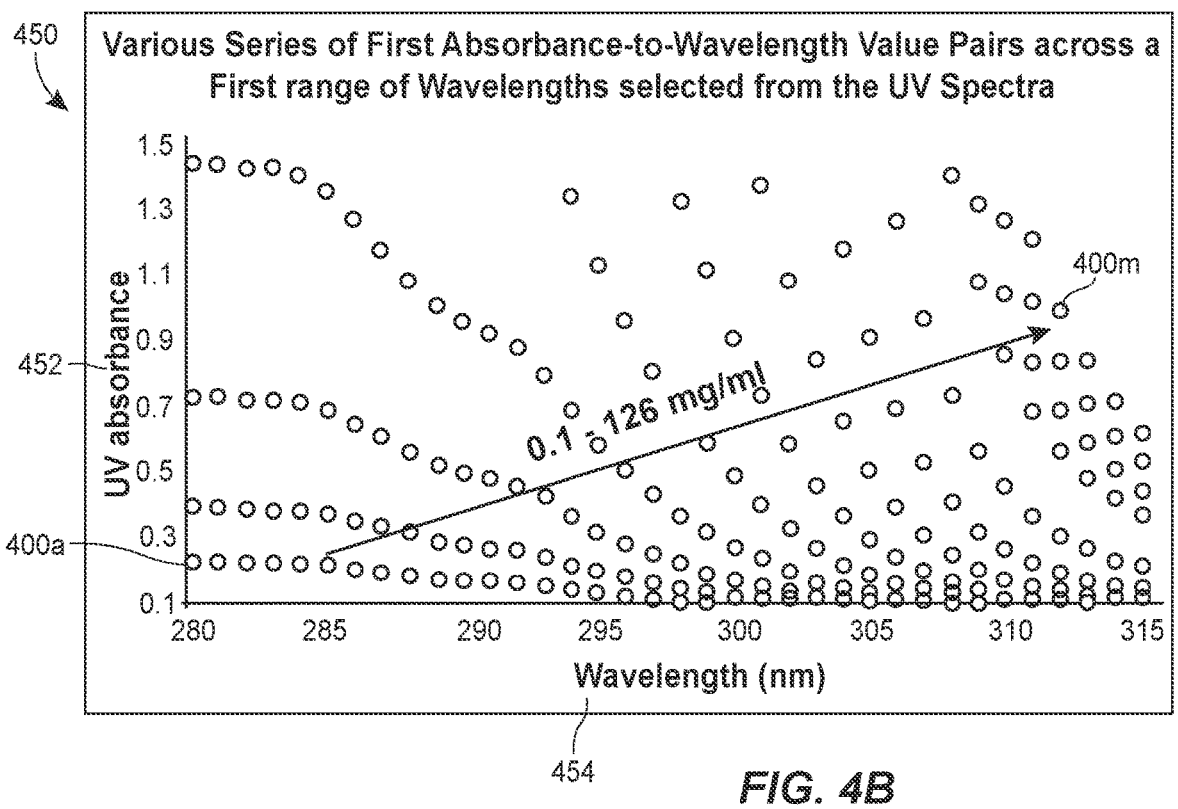
FIG. 4B illustrates a diagram representing various series of first absorbance-to-wavelength value pairs across a first range of wavelengths selected from the UV spectra, in accordance with various embodiments disclosed herein.

In particular, FIG. 4B illustrates a diagram 450 representing various series of first absorbance-to-wavelength value pairs across a first range of wavelengths (e.g., wavelength axis 454) selected from the UV spectra, in accordance with various embodiments disclosed herein. As shown by FIG. 4B, absorbance-to-wavelength value pairs of each of standard protein samples (e.g., standard protein samples 140s) 400a to 400m are shown, however some absorbance-to-wavelength value pairs have been filtered by the standard wavelength data filter (e.g., at block 208) as described herein. In particular, FIG. 4B illustrates an embodiment where a standard wavelength data filter was applied to absorbance-to-wavelength value pairs plotted across the single-wavelength light beam range 200 to 400 (nm) of FIG. 4A.

As shown by FIG. 4B, a standard wavelength data filter (e.g., at block 208) has been applied to the single-wavelength light beam range 200 to 400 (nm) of FIG. 4A to select a first range of wavelengths 280 to 315 (nm) of FIG. 4B. The first range of wavelengths range of wavelengths 280 to 315 (nm) is depicted across wavelength axis 454 of FIG. 4B. Thus, the first range of wavelengths range of wavelengths 280 to 315 (nm) of FIG. 4B has been selected from the single-wavelength light beam range 200 to 400 (nm) of FIG. 4A.

In addition, in the embodiment of FIG. 4B, the standard wavelength data filter (e.g., at block 208) has been applied to select each first series of first absorbance-to-wavelength value pair based on UV absorbance values within a first filter range of UV absorbance values (e.g., (e.g., UV absorbance axis 452). The first filter range of UV absorbance values 0.1 to 1.5 is depicted across UV absorbance axis 452 of FIG. 4B. Thus, first filter range of UV absorbance value range 0.1 to 1.5 of FIG. 4B has been selected from the UV absorbance value range 0 to 7 of FIG. 4A. Accordingly, FIG. 4B generally illustrates a filtered UV spectra of calibration standards, in particular, showing filtered UV spectra of protein calibration standards within the limited ranges of wavelength values 280 to 315 nm and absorbance values 0.1 to 1.5. When compared with FIG. 4A, the filtered values (wavelength values 280 to 315 nm and absorbance values 0.1 to 1.5) generally include those absorbance-to-wavelength value pairs, across each of the standard protein samples (e.g., 400a and standard protein sample 400m) that are not collapsed with respect to, or are on top of, each other as shown by diagram 400.

In the examples of FIGS. 4A and 4B, the standard protein samples (e.g., standard protein samples 140s) are protein standard solutions in the range of 0.1 to 126 mg/mg, which is illustrated in FIG. 4B. This is further illustrated in the example computer program listing of FIGS. 3A and 3B at Code Section 2, where the standard protein sample values are set to a corresponding range. However, wider ranges of such standard protein samples (e.g., standard protein samples 140s)/protein standard solutions are contemplated herein, for example where the set of standard protein samples may be protein standard solutions in the range of 0.1 to 220 milligrams (mg) per milliliter (ml).

With respect to FIG. 2A, at block 210, UV based imaging method 200 includes generating, with a processor (e.g., processor 124 or remote processor 154), a multi-wavelength calibration model. The multi-wavelength calibration model is based on the standard set of wavelength data and its various absorbance-value pairs of each standard protein sample. In certain embodiments, where such data was filtered (e.g., at block 208), the multi-wavelength calibration model is based on each of the first series of first absorbance-to-wavelength value pairs of the standard set of wavelength data.

FIG. 5A illustrates a diagram 500 representing a multi-wavelength calibration model 501 comprised of single-wavelength calibration models (i.e., "calibration curves"), in accordance with various embodiments disclosed herein. In the embodiment of FIG. 5A, the multi-wavelength calibration model 501 is comprised of single-wavelength calibration models across the UV spectra of FIG. 4B. This includes a model for each of the wavelengths from 280 nm to 315 nm. For example, diagram 500 identifies single-wavelength calibration models 501s280 (which is a single-wavelength model for wavelength 280 nm), 501s294 (which is a single-wavelength model for wavelength 294 nm), and 501s300 (which is a single-wavelength model for wavelength 300 nm). Each single-wavelength calibration model is generated to predict, for a particular wavelength (e.g., 280 nm, 294 nm, and 300 nm), a protein concentration value (across the range of protein concentration values of protein concentration axis 504) for a given UV absorbance value (across the range of UV absorbance values of UV absorbance axis 502). UV absorbance axis 502 of FIG. 5A corresponds to UV absorbance axis of FIG. 4B. Thus, a protein concentration prediction, for a given wavelength of the UV spectra, may made by inputting a UV absorbance value into the corresponding single-wavelength calibration model or calibration curve for that wavelength of the UV spectra. The predictions may be used to determine unknown protein concentrations of unknown protein samples (e.g., unknown protein samples 140u) as described herein.

In the embodiment of FIG. 5A, a linear regression algorithm was used to determine each of the single-wavelength calibration models (e.g., 501s280, 501s294, and 501s300). Each such model includes a y-intercept value and a slope value, which are used to predict protein concentrations. The y-intercept value and slope values are generally determined as constant values, where the slope value is applied to a provided UV absorbance value, the result of which is added to the y-intercept value, to produce a corresponding protein concentration prediction or value. Diagram 500 of FIG. 5A illustrates various predictions or values of protein concentrations (across the protein concentration axis 504) for each of the single-wavelength calibration models as different UV absorbance values are provided to each of the respective single-wavelength calibration models (e.g., 501s280, 501s294, and 501s300). In this way, the whole of the single-wavelength calibration models comprise a multi-wavelength calibration model that can accept absorbance values for each wavelength and UV absorbance value as determined and described for FIGS. 4A and 4B.

FIG. 5B illustrates a diagram 550 representing slopes 560s and y-intercepts 560y of the various single-wavelength calibration models (e.g., single-wavelength calibration models 501s280, 501s294, and 501s300) of FIG. 5A, in accordance with various embodiments disclosed herein. FIG. 5B shows plots of pairs of slope values 560s and y-intercept values 560y at each wavelength between 280 nm and 315 nm across wavelength axis 554. FIG. 5B includes the same ranges of UV absorbance values (e.g., UV absorbance axis 552) and the same ranges of wavelength values (e.g., wavelength axis 554) as FIG. 5A. The pairs of slope 560s and y-intercept values 560y correspond to single-wavelength calibration models (e.g., single-wavelength calibration models 501s280, 501s294, and 501s300) of FIG. 5A. For example, as shown by FIG. 5B, slope value 562a corresponds to y-intercept value 562b of the 280 nm wavelength which corresponds to single-wavelength calibration model 501s280. Likewise, as shown by FIG. 5B, slope value 564a corresponds to y-intercept value 564b of the 290 mn wavelength which corresponds to single-wavelength calibration model 501s290. The y-axis (UV absorbance axis 552) shows the amount of UV absorbance that a given slope value or y-intercept value contributes to any given prediction of a single-wavelength calibration model.

Accordingly, at least with respect to the embodiment of FIG. 5B, multi-wavelength calibration model 501 of FIG. 5A may be generated and comprised of a series of single-wavelength calibration models for each of the first range of wavelengths (e.g., wavelengths 280 nm to 315 nm as described for FIG. 4B) selected from the range of the single-wavelength light beams (e.g., wavelengths 200 nm to 400 nm as described for FIG. 4A), where each single-wavelength calibration model (e.g., 501s280, 501s294, and 501s300) includes a slope value 560s and a y-intercept value 560y corresponding to UV absorbance of particular single wavelength (e.g., wavelengths 280 nm, 294 nm, and 300 nm, respectively). By inputting a wavelength value and a UV absorbance value, a processor (e.g., processor 124 and/or remote processor 154) implementing multi-wavelength calibration model 501 may select the corresponding single-wavelength calibration model to correctly and accurately predict a protein concentration value.

The example computer program listing of FIGS. 3A and 3B illustrates generation of the single-wavelength calibration models for each of the first range of wavelengths (e.g., wavelengths 280 nm to 315 nm as described for FIG. 4B). For example, at Code Section 8, after standard wavelength data is filtered, a liner regression algorithm (LinearRegression.fit) is executed by a processor (e.g., processor 124 or remote processor 154) for the data of each standard protein sample, which results in a coefficient value (i.e., a slope value) and an intercept value (i.e., a y-intercept value) generated for a single-wavelength calibration model at a particular wavelength. Thus, each single-wavelength calibration model (e.g., 501s280, 501s294, and 501s300) may be generated in this fashion. The single-wavelength calibration models may be stored in a memory (e.g., memory 121 or remote memory 159), and may together be accessed (e.g., via a wrapper API or as a data structure via a database) as a comprehensive multi-wavelength calibration model as described herein. In the embodiment of FIGS. 3A and 3B, each single-wavelength calibration model includes a quality or fit score of a certain threshold. For example, in Code Section 3, only single-wavelength calibration model with a minimum quality or fit value of 0.99 may be included in the multi-wavelength calibration model. In this way, the multi-wavelength calibration model 501 maintains and uses a high-quality set of predictive models with accurate predictive capabilities.

In the above embodiments of FIGS. 5A and 5B, single-wavelength calibrations are generated via linear regression and are compiled to generated multi-wavelength calibration model 501. However, other predictive technologies or techniques may be used. For example, a machine-learning model, may be trained using a supervised or unsupervised machine learning program or algorithm. The machine learning program or algorithm may employ a neural network, which may be a convolutional neural network, a deep learning neural network, or a combined learning module or program that learns in two or more features or feature datasets in a particular area of interest. The machine learning programs or algorithms may also include natural language processing, semantic analysis, automatic reasoning, regression analysis, support vector machine (SVM) analysis, decision tree analysis, random forest analysis, K-Nearest neighbor analysis, naïve Bayes analysis, clustering, reinforcement learning, and/or other machine learning algorithms and/or techniques. Machine learning may involve identifying and recognizing patterns in existing data (such as UV absorbance values of standard protein samples (e.g., standard protein samples 140s) across a UV spectra) in order to facilitate making predictions for subsequent data (to predict unknown concentrations of unknown protein samples (e.g., unknown protein samples 140u) as described herein).

Machine learning model(s), such as those of a machine-learning model described above herein, may be created and trained based upon example (e.g., "training data,") inputs or data (which may be termed "features" and "labels") in order to make valid and reliable predictions for new inputs, such as testing level or production level data or inputs. In supervised machine learning, a machine learning program operating on a server, computing device, or otherwise processor(s), may be provided with example inputs (e.g., "features") and their associated, or observed, outputs (e.g., "labels") in order for the machine learning program or algorithm to determine or discover rules, relationships, or otherwise machine learning "models" that map such inputs (e.g., "features") to the outputs (e.g., labels), for example, by determining and/or assigning weights or other metrics to the model across its various feature categories. Such rules, relationships, or otherwise models may then be provided subsequent inputs for the model, executing on the server, computing device, or otherwise processor(s), to predict, based on the discovered rules, relationships, or model, an expected output.

In unsupervised machine learning, the server, computing device, or otherwise processor(s), may be required to find its own structure in unlabeled example inputs, where, for example multiple training iterations are executed by the server, computing device, or otherwise processor(s) to train multiple generations of models until a satisfactory model, e.g., a model that provides sufficient prediction accuracy when given test level or production level data or inputs, is generated. The disclosures herein may use one or both of such supervised or unsupervised machine learning techniques.

Accordingly, the single-wavelength calibration models of the multi-wavelength calibration model, or the multi-wavelength calibration model itself, may be trained with the wavelength data of the standard protein samples (e.g., standard protein samples 140s), where the wavelength values and UV absorbance values (e.g., of the various absorbance-to-wavelength value pairs as described herein) are input as feature data, and where protein concentration values of the standard protein samples (e.g., standard protein samples 140s) may be used as label data. The trained single-wavelength calibration models of the multi-wavelength calibration model, or the multi-wavelength calibration model, may then be used to predict protein concentrations of samples with unknown concentrations as describe herein.

With respect to FIG. 2A, UV based imaging method 200 includes the processor (e.g., processor 124 or remote processor 154) receiving (at block 212) an unknown set of wavelength data (e.g., wavelength data 118) as recorded by a detector (e.g., detector 114) for each unknown protein sample of a set of unknown protein samples (e.g., unknown protein samples 140u).

In some embodiments, the unknown set of wavelength data (e.g., wavelength data 118) may be received as comma separated value (CSV) data. In other embodiments, the standard set of wavelength data may be received in a database format, extensible markup language (XML), JavaScript Object Notation (JSON), or other data or textual format as described herein. In the embodiment computer program listing of FIGS. 3A and 3B, for example, at Code Sections 8 and 10, wavelength data of unknown protein samples (e.g., unknown protein samples 140u) is read into memory (e.g., memory 121 or remote memory 159) by a processor (e.g., processor 124 or remote processor 154) as CSV data, where a user enters the data as a file containing the wavelength data of unknown protein samples (e.g., unknown protein samples 140u).

The unknown set of wavelength data (e.g., wavelength data 118) may include, for each unknown protein sample, a second series of second absorbance-to-wavelength value pairs across a second range of wavelengths selected from the range of the single-wavelength light beams. Each second absorbance-to-wavelength value pair may comprise a UV absorbance value and a wavelength value. The unknown set of wavelength data may be captured and/or measured in the same manner as described for the standard protein samples (e.g., standard protein samples 140s) of FIG. 4A as described herein.

UV based imaging method 200 continues (214) as shown in FIGS. 2A and 2B, where, at block 216 a processor (e.g., processor 124 or remote processor 154) determines whether to filter the unknown set of wavelength data. The determination may be made based on the range of the wavelength data detected (e.g., by detector 114), where some datasets include wide wavelength ranges. If no filter is applied, UV based imaging method 200 proceeds to block 220.

At block 218, however, an unknown wavelength data filter is applied. Unknown wavelength data filter may comprise a set of program instructions stored in a memory of UV imaging system 100, for example, in memory 121 or remote memory 154. In the computer program listing of FIGS. 3A and 3B, for example, pseudo-Python instructions illustrate an embodiment an unknown wavelength data filter (Code Section 7) for removing data points from the original single-wavelength light range and original UV absorbance value ranges as measured by detector 114 to ensure an optimal data quality used to train calibration models as described herein. In the example of FIG. 3A, Code Section 7 applies filtering criteria set, as user-defined variables (Code Section 4), to allow flexible manipulation of the filtered ranges. For example, as shown in Code Section 4, filtering criteria for unknown protein samples (e.g., unknown protein samples 140u) is configured to select data points with UV absorbance values of 0.2 to 1.2 for the wavelength range of 280 to 315 nm.

At block 218, a processor (e.g., processor 124 or remote processor 154) implements the unknown wavelength data filter against a range of the single-wavelength light beams to select or limit a second range of wavelengths. In addition, the processor may implement the unknown wavelength data filter to select or limit each second series of second absorbance-to-wavelength value pair based on UV absorbance values within a second filter range of UV absorbance values. For example, application of the unknown wavelength data filter (e.g., at block 218) yields diagram 600 of FIG. 6 which represents a limited or filtered set of data ranges (in both wavelength and absorbance values, i.e., absorbance-to-wavelength value pairs) of the unknown protein sample data detected and/or received at block 212.

Figure 6:
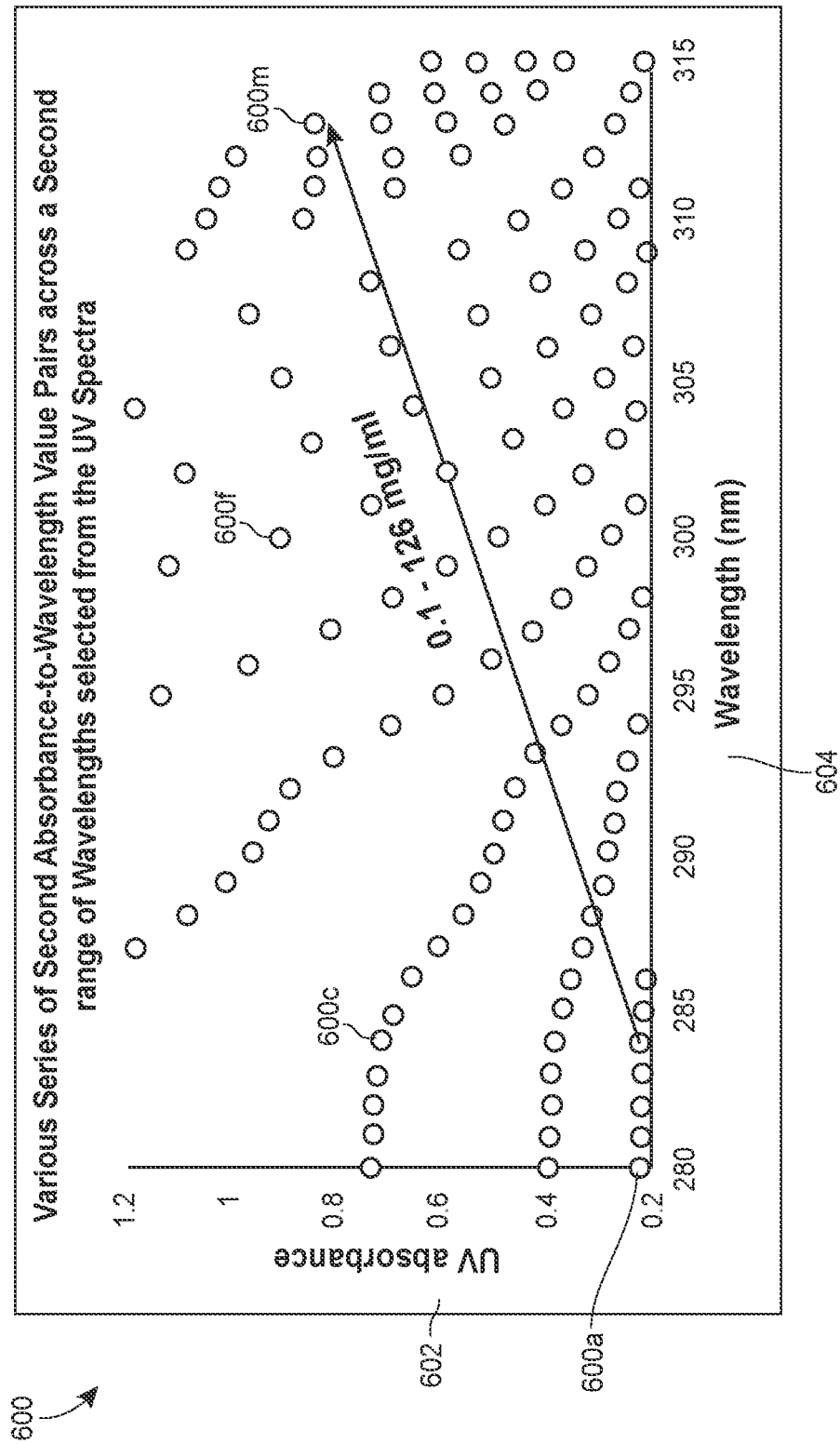
FIG. 6 illustrates a diagram representing various series of second absorbance-to-wavelength value pairs across a second range of wavelengths selected from the UV spectra, in accordance with various embodiments disclosed herein.

In particular, FIG. 6 illustrates a diagram 600 represents various series of second absorbance-to-wavelength value pairs across a second range of wavelengths (e.g., wavelength axis 604) selected from the UV spectra, in accordance with various embodiments disclosed herein. FIG. 6 is similar to FIG. 4B but shows filtered data for unknown protein samples (e.g., unknown protein samples 140u). As shown by FIG. 6, absorbance-to-wavelength value pairs of 13 individual unknown protein samples (e.g., unknown protein samples 140u) are represented by plots for unknown protein samples 600a to 600m (including for each of 600a, 600c, 600f, and 600m). In the embodiment of FIG. 6, some absorbance-to-wavelength value pairs have been filtered by the unknown wavelength data filter (e.g., at block 218) as described herein, and are not shown in diagram 600. In particular, FIG. 6 illustrates an embodiment where an unknown wavelength data filter was applied to absorbance-to-wavelength value pairs plotted across a UV spectrum used to detect the unknown wavelength data (e.g., wavelength data 118).

As shown by FIG. 6, an unknown wavelength data filter (e.g., at block 218) has been applied to select a second range of wavelengths 280 nm to 315 nm of FIG. 6. The second range of wavelengths range of wavelengths 280 nm to 315 nm is depicted across wavelength axis 604 of FIG. 6. In various embodiments, the second range of wavelengths range of wavelengths 280 to 315 (nm) of FIG. 6 can be selected from the single-wavelength light beam range 200 nm to 400 nm of FIG. 4A.

In addition, in the embodiment of FIG. 6, the unknown wavelength data filter (e.g., at block 218) has been applied to select each second series of second absorbance-to-wavelength value pairs based on UV absorbance values within a second filter range of UV absorbance values (e.g., UV absorbance axis 602). The second filter range of UV absorbance values 0.2 to 1.2 is depicted across UV absorbance axis 602 of FIG. 6. Thus, second filter range of UV absorbance value range 0.2 to 1.2 of FIG. 6 has been selected from the UV absorbance value range 0 to 7 of FIG. 4A. Accordingly, FIG. 6 illustrates a filtered UV spectra of unknown protein samples (e.g., unknown protein samples 140u), in particular, showing filtered UV spectra of unknown protein samples (e.g., unknown protein samples 140u) within the limited ranges of wavelength values 280 to 315 nm and absorbance values 0.2 to 1.2.

In the example of FIG. 6, the unknown protein samples (e.g., unknown protein samples 140u) are protein solutions in the range of 0.1 to 126 mg/mg. The protein solutions for the unknown protein samples (e.g., unknown protein samples 140u), at least for the embodiment of FIG. 6, use the same protein solution range as described above for FIGS. 4A and 4B.

With respect to FIG. 2B, at block 220 of UV based imaging method 200, a processor (e.g., processor 124 or remote processor 154) determines, with the multi-wavelength calibration model, for each unknown protein sample of the set of unknown protein samples (e.g., unknown protein samples 140u), a plurality of protein concentration values. Each protein concentration value of the plurality of protein concentration values may correspond to the second range of wavelengths (e.g., range 280 nm to 315 nm of FIG. 6) selected from the range of the single-wavelength light beams (e.g., range 200 nm to 400 nm of FIG. 4A).

In some embodiments, at least one unknown protein sample of the set of unknown protein samples (e.g., unknown protein samples 140u) may comprise a protein therapeutic. In such embodiments, the protein therapeutic may be any one of an antibody, an antigen-binding antibody fragment, an antibody protein product, a Bi-specific T cell engager (BiTE®) molecule, a bispecific antibody, a trispecific antibody, an Fc fusion protein, a recombinant protein, and an active fragment of a recombinant protein.

In the example computer program listing of FIGS. 3A and 3B, a processor (e.g., processor 124 or remote processor 154) determines, with the multi-wavelength calibration model, for each unknown protein sample of the set of unknown protein samples (e.g., unknown protein samples 140u), a plurality of protein concentration values. In particular, in Code Section 10, a "calc_unk" code function is invoked. The calc_unk code function (Code Section 9) reads in the wavelength data (e.g., wavelength data 118) for each unknown protein sample of the set of unknown protein samples (e.g., unknown protein samples 140u) as CSV data. The "calc_unk" code function (Code Section 9) then determines, with the multi-wavelength calibration model (i.e., stored in memory in variable "df") the plurality of protein concentration values, which is stored in a "conc" variable. In the embodiment of FIGS. 3A and 3B, the "calc_unk" code function (Code Section 9) is configured to generate an enhanced prediction by summing the values (e.g., the various values of the "conc" variables for each individual predicted concentration) and producing an average predicted value, across all protein concentration predictions, of the second range of wavelengths (e.g., the range of 280 nm to 315 nm of FIG. 6).

Figure 7:
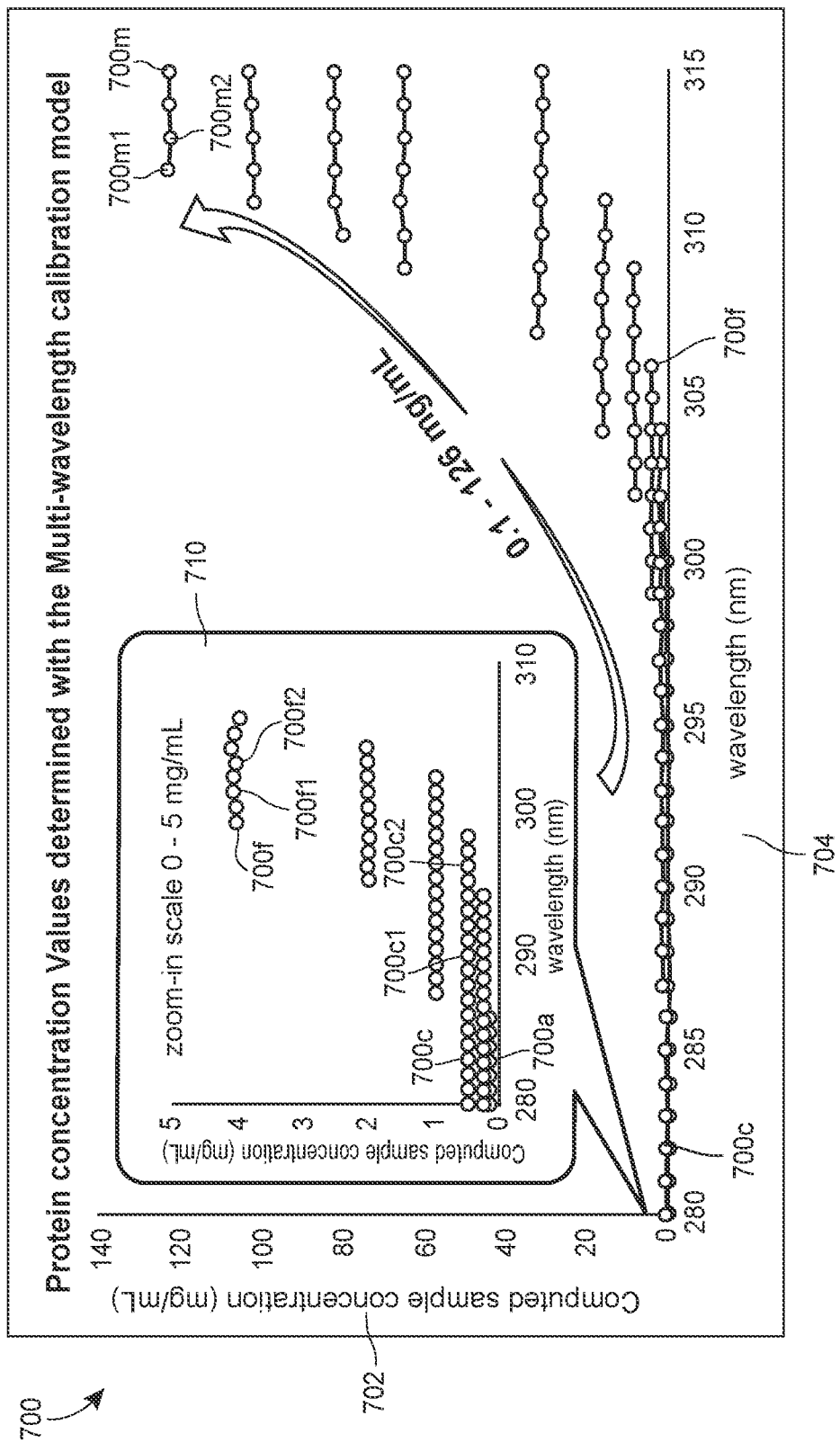
FIG. 7 illustrates a diagram representing protein concentration values determined with the multi-wavelength calibration model of FIG. 5A, in accordance with various embodiments disclosed herein.

FIG. 7 illustrates a diagram 700 depicting protein concentration values determined with the multi-wavelength calibration model 501 of FIG. 5A, in accordance with various embodiments disclosed herein. In the embodiment of FIG. 7, diagram 700 represents application of multi-wavelength calibration model 501 to the second range of wavelengths (e.g., range 280 to 315 (nm) of FIG. 6) as filtered for the unknown protein samples (e.g., unknown protein samples 140u). Protein concentration values are depicted in diagram 700 for each applicable wavelength.

As shown by FIG. 7, unknown protein samples (e.g., unknown protein samples 140u) are represented as unknown protein samples 700a to 700m and are plotted as protein concentration values along protein concentration axis 702 (y-axis) and as wavelength values along wavelength axis 704 (x-axis). Wavelength axis 704 (x-axis) includes the same wavelength values (i.e., the range of 280 nm to 315 nm) as wavelength axis 604 of FIG. 6. Each of unknown protein samples 700a, 700c, 700f, and 700m correspond to unknown protein samples 600a, 600c, 600f, and 600m of FIG. 6, as described herein.

FIG. 7 includes a zoomed portion 710 depicting several of the unknown protein samples, including 700a and 700c, on magnified scale. That is, zoomed portion 710 is equivalent to diagram 700, just at a different scale. In particular, zoomed portion 710 shows protein concentration values on a magnified range of 0 to 5 mg/ml where several of the unknown protein samples, including 700a, 700c, and 700f, have protein concentration values within that range. Each of unknown protein samples 700a to 700f depicted by zoomed portion 710 corresponds to unknown protein samples 700a to 700f depicted by diagram 700.

Each point of a given unknown protein sample (e.g., 700a to 700m) provides a prediction of a protein concentration value for a given sample at a given wavelength. For example, as illustrated by zoomed portion 710, unknown protein sample 700c includes two points 700c1 and 700c2. Zoomed portion 710 represents that for point 700c1, multi-wavelength calibration model 501 predicted that unknown protein sample 700c has a protein concentration value prediction of approximately 0.5 at wavelength value of approximately 290 nm. Likewise, zoomed portion 710 represents that for point 700c2, multi-wavelength calibration model 501 predicted that unknown protein sample 700c has a protein concentration value prediction of approximately 0.5 at wavelength value of approximately 298 nm.

As a further example, as illustrated by zoomed portion 710, unknown protein sample 700f includes two points 700f1 and 700f2. Zoomed portion 710 represents that for point 700f1, multi-wavelength calibration model 501 predicted that unknown protein sample 700f has a protein concentration value prediction of approximately 4.0 at wavelength value of approximately 300 nm. Likewise, zoomed portion 710 represents that for point 700f2, multi-wavelength calibration model 501 predicted that unknown protein sample 700f has a protein concentration value prediction of approximately 3.8 at wavelength value of approximately 303 nm.

As an additional example, as illustrated by diagram 700, unknown protein sample 700m includes two points 700m1 and 700m2. Diagram 400 represents that for point 700m1, multi-wavelength calibration model 501 predicted that unknown protein sample 700m has a protein concentration value prediction of approximately 122 at wavelength value of approximately 312 nm. Likewise, diagram 700 represents that for point 700m2, multi-wavelength calibration model 501 predicted that unknown protein sample 700m has a protein concentration value prediction of approximately 121 at wavelength value of approximately 313 nm.

In this way, as represented by FIG. 7, a multi-wavelength calibration model (e.g., multi-wavelength calibration model 501), may input a series of absorbance-to-wavelength value pairs (e.g., the second series of second absorbance-to-wavelength value pairs as described for FIG. 6) to predict each plurality of protein concentration values. In some embodiments, only the wavelength values or only the absorbance values of each of the absorbance-to-wavelength value pairs need be provided as input into multi-wavelength calibration model 501 to generate the predictions. Accordingly, wavelength value(s) and/or absorbance value(s) a particular wavelength (corresponding to a single-wavelength model) may be input to predict the protein concentration value for that particular absorbance value and/or for that particular wavelength.

With respect to FIG. 2B, at block 222 of UV based imaging method 200, a processor (e.g., processor 124 or remote processor 154) determines whether to generate an enhanced prediction based on the plurality of protein concentration values that were determined by multi-wavelength calibration model 501. If no enhanced prediction is to be made, UV based imaging method 200 proceeds to block 226.

At block 224 of UV based imaging method 200, a processor (e.g., processor 124 or remote processor 154) has determined to generate an enhanced prediction. Such determination may be made, for example, by setting a threshold predictive quality value (for example in the program instructions executed by the processor), requiring that the prediction be of a sufficient quality or fit. This is demonstrated, for example, by Code Section 3 of FIG. 3A. This is also demonstrated in Code Section 9 of FIG. 3B, where each protein concentration value is automatically averaged, thereby creating an enhanced prediction, with enhanced precision, across a range of the wavelength values (e.g., the second range of wavelengths as described for FIGS. 6 and 7). In other embodiments, a flag may be set in, or provided to, the program instructions or code to indicate that the enhanced prediction is to be generated. Thus, in various embodiments, generation of the enhanced prediction may comprise averaging (or otherwise manipulating) each protein concentration value of the plurality of protein concentration values corresponding to the second range of wavelengths. The enhanced prediction may include an average, median, derivative, or other manipulation of the protein concentration values determined by a multi-wavelength calibration model (e.g., multi-wavelength calibration model 501).

The enhanced prediction takes advantage of the overlapping the ranges of wavelengths and predicted concentration values of each of the samples (e.g., unknown protein samples 700a to 700m) as illustrated by FIG. 7, and provides an overlapped concentration measurement, which results in enhanced precision compared with the single predictive points (e.g., points 700c1 or 700c2) alone. In various embodiments, a multi-wavelength calibration model (e.g., multi-wavelength calibration model 501) may be updated with, or configured to compute and/or output (as shown in Code Section 9 of FIG. 3B) the enhanced prediction.

With respect to FIG. 2B, at block 226 of UV based imaging method 200, a processor (e.g., processor 124 or remote processor 154) uses the multi-wavelength calibration model, either as generated at block 220 or as further updated or configured by the enhanced prediction (e.g., as manipulated at block 224) to monitor or measure protein concentration of a protein-related product. In various embodiments, the protein-related product is a therapeutic product.

Figure 8:
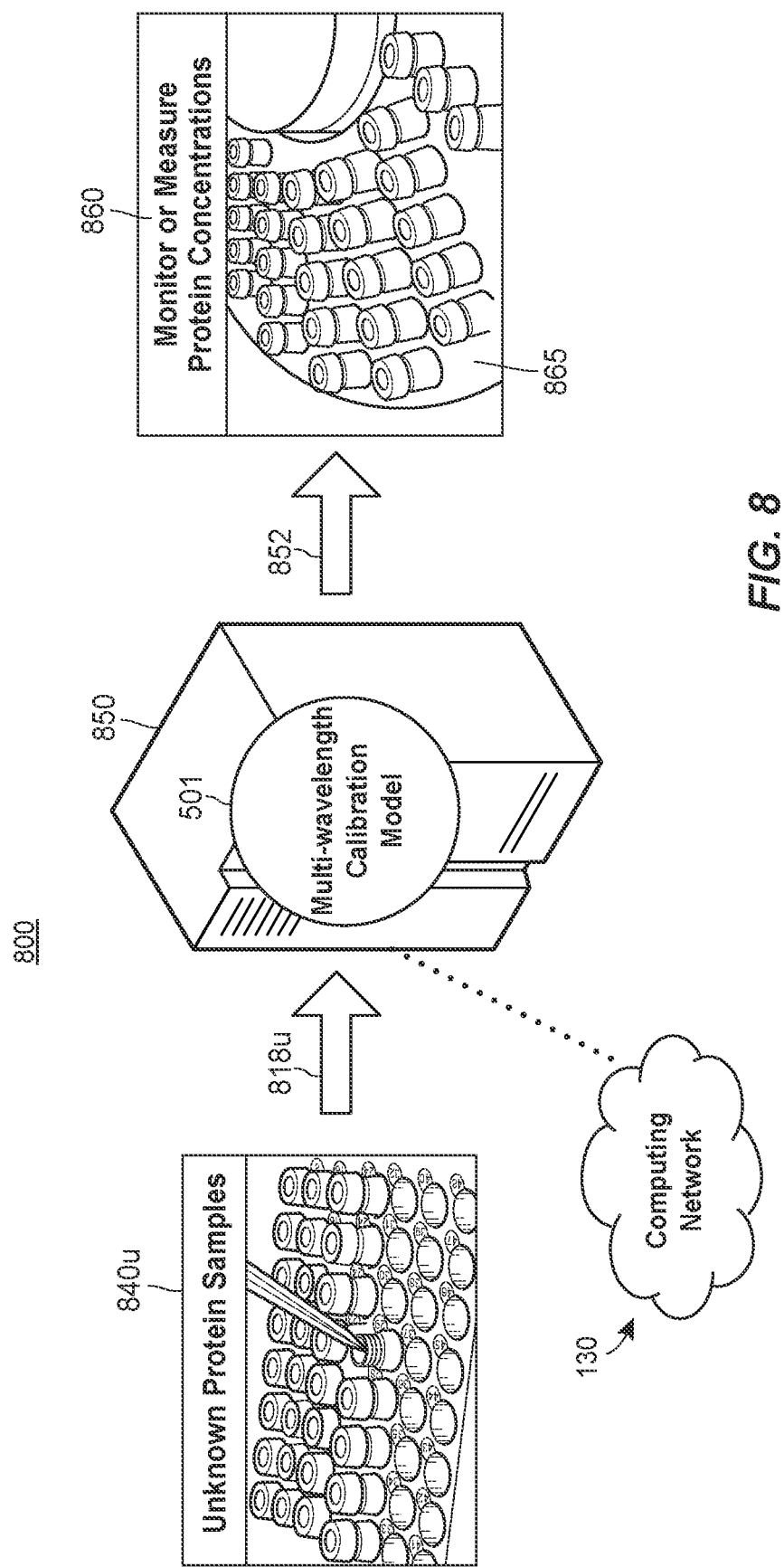
FIG. 8 illustrates a flow diagram depicting application of the multi-wavelength calibration model of FIG. 5A to monitor or measure protein concentration of protein-related products, in accordance with various embodiments disclosed herein.

FIG. 8 illustrates a flow diagram 800 depicting application of the multi-wavelength calibration model 501 of FIG. 5A to monitor or measure protein concentration of protein-related products 860, in accordance with various embodiments disclosed herein. As illustrated by diagram 800, a batch of unknown protein samples 840u is scanned by a UV imaging device (e.g., UV imaging device 101 as described herein) to produce wavelength data 818u for each of the unknown protein samples 840u. The unknown protein samples 840u may be unknown protein samples 140u or may be a new set of samples. Wavelength data 818u is the same data or same type of data as described herein for FIGS. 1, 2A, 2B, etc., with respect to wavelength data 118. Wavelength data 818u may be input into multi-wavelength calibration model 501, which would have been previously generated from standard protein sample data, as described herein with respect to FIGS. 2B, 2B, 3A, 3B, 4, and 5A, etc.

In the embodiment of FIG. 8, multi-wavelength calibration model 501 is loaded into a memory (not shown) of process control device 850. Process control device 850 includes a processor (not shown) for implementing multi-wavelength calibration model 501 to monitor or measure protein concentration of protein-related products 860. In some embodiments, process control device 850 receives multi-wavelength calibration model 501 from the UV imaging device 101 and/or computing device 151 via computer network 130, such as via transmission of data packets via transmission control protocol and internet protocol (TCP/IP) or via other such similar protocols.

Process control device 850 may apply multi-wavelength calibration model 501 by outputting a prediction 852 (either an enhanced prediction or a prediction based on one or more of the computed protein concentration values of each of the standard protein samples as described herein). Prediction 852 may then be used for monitoring or measuring protein concentration of protein-related products 860. For example, in some embodiments, prediction 852, or signals or data transmission produced based on prediction 852, may be transmitted or otherwise provided to sub-devices (not shown) of a process control or manufacturing system, such as field devices communicatively coupled to process control device 850 via a process control network, for monitoring or measuring protein concentration of protein-related products 860. Accordingly, prediction 852 may be output from process control device 850 and used to monitor, test, measure, or develop protein concentrations in end-use products. In one embodiment, for example, prediction 852 may be used to monitor or measure protein concentration 860 of protein-related products 865 during manufacture of the protein-related products 865. Protein-related products 865 may be products developed via an assembly or automated system in a process control plant with process control device 850. By way of example, based on the measured protein concentration, the protein concentration of the protein-related product may be increased or decreased to fall within a specified range of protein concentration. By way of example, a batch of protein-related product may be accepted or rejected depending on whether the measured protein concentration falls within or outside of (respectively) a specified range. Because of the robustness of multi-wavelength calibration model 501, as implemented on process control device 850, protein concentration of protein-related products 865 may be measured or monitored in a wide range of UV spectra, including the ranges of UV spectra as described herein.

In a further example, prediction 852 of multi-wavelength calibration model 501 as provided by process control device 850 may be used to monitor or measure protein concentration 860 of protein-related products 865 against, or to compare with, known specifications for the protein-related product. The known specifications may be defined, for example, by the standard protein samples 140s. In such embodiments, Process control device 850 may apply prediction 852 to protein-related products 865 to compare known specifications and measure compliance with regulatory requirements, efficacy or quality thresholds, or other regulatory or quality concerns.

Accordingly, as provided herein, the UV based imaging systems and methods of the present disclosure improve over the limitations of currently known instruments and methods. The UV based imaging systems and methods described herein overcome the linearity limitations of the Beer-Lampert Law by instead generating and applying a unique multi-wavelength calibration model 501 calibrated with a set of protein sample standards. In addition, unlike other instruments, such as mechanical path length instruments which scan an extended linear protein concentration range by mechanical means, the UV based imaging systems and methods of the present disclosure generate and use a multi-wavelength calibration model (e.g., multi-wavelength calibration model 501) which avoid issues of mechanical error.

Therapeutic proteins come in many forms and formats; the method is agnostic to the type of therapeutic protein. In the case of antibodies as therapeutic proteins, for example, the architecture of antibodies has been exploited to create a growing range of alternative formats that span a molecular-weight range of at least about 12-150 kDa and has a valency (n) range from monomeric (n=1), to dimeric (n=2), to trimeric (n=3), to tetrameric (n=4), and potentially higher; such alternative formats are referred to herein as "antibody protein products". Antibody protein products include those based on the full antibody structure and those that mimic antibody fragments which retain full antigen-binding capacity, e.g., scFvs, Fabs and VHH/VH (discussed below). The smallest antigen binding antibody fragment that retains its complete antigen binding site is the Fv fragment, which consists entirely of variable (V) regions. A soluble, flexible amino acid peptide linker is used to connect the V regions to a scFv (single chain fragment variable) fragment for stabilization of the molecule, or the constant (C) domains are added to the V regions to generate a Fab fragment [fragment, antigen-binding]. Both scFv and Fab fragments can be easily produced in host cells, e.g., prokaryotic host cells. Other antibody protein products include disulfide-bond stabilized scFv (ds-scFv), single chain Fab (scFab), as well as di- and multimeric antibody formats like dia-, tria- and tetra-bodies, or minibodies (miniAbs) that comprise different formats consisting of scFvs linked to oligomerization domains. The smallest fragments are VHH/VH of camelid heavy chain Abs as well as single domain Abs (sdAb). The building block that is most frequently used to create novel antibody formats is the single-chain variable (V)-domain antibody fragment (scFv), which comprises V domains from the heavy and light chain (VH and VL domain) linked by a peptide linker of —15 amino acid residues. A peptibody or peptide-Fc fusion is yet another antibody protein product. The structure of a peptibody consists of a biologically active peptide grafted onto an Fc domain. Peptibodies are well-described in the art. See, e.g., Shimamoto et al., mAbs 4(5): 586-591 (2012).

Other antibody protein products include a single chain antibody (SCA); a diabody; a triabody; a tetrabody; bispecific or trispecific antibodies, and the like. Bispecific antibodies can be divided into five major classes: BsIgG, appended IgG, BsAb fragments, bispecific fusion proteins and BsAb conjugates. See, e.g., Spiess et al., Molecular Immunology 67(2) Part A: 97-106 (2015).

In exemplary aspects, the therapeutic protein comprises any one of these antibody protein products. In exemplary aspects, the therapeutic protein comprises any one of an scFv, Fab VHH/VH, Fv fragment, ds-scFv, scFab, dimeric antibody, multimeric antibody (e.g., a diabody, triabody, tetrabody), miniAb, peptibody VHH/VH of camelid heavy chain antibody, sdAb, diabody; a triabody; a tetrabody; a bispecific or trispecific antibody, BsIgG, appended IgG, BsAb fragment, bispecific fusion protein, and BsAb conjugate.

In exemplary aspects, the therapeutic protein is a bispecific T cell engager (BiTE®) molecule. A BiTE® molecule is a bispecific antibody construct or bispecific fusion protein comprising two antibody binding domains (or targeting regions) linked together. BiTE® molecules are constructed of two single chain variable fragments (scFv) connected in tandem by a flexible linker (scFc-scFc, Huehls et al, 2015). One arm of the molecule is engineered to bind with a protein found on the surface of cytotoxic T cells, and the other arm is designed to bind to a specific protein found primarily on tumor cell. When both targets are engaged, the BiTE® molecule forms a bridge between the cytotoxic T cell and the tumor cell, which enables the T cell to recognize the tumor cell and fight it through an infusion of toxic molecules. The tumor-binding arm of the molecule can be altered to create different BiTE® antibody constructs that target different types of cancer. The term "binding domain" in regard to a BiTE® molecule refers to a domain which (specifically) binds to/interacts with/recognizes a given target epitope or a given target site on the target molecules (antigens). The structure and function of the first binding domain (recognizing the tumor cell antigen), and preferably also the structure and/or function of the second binding domain (cytotoxic T cell antigen), is/are based on the structure and/or function of an antibody, e.g. of a full-length or whole immunoglobulin molecule. For example, the BiTE® molecule comprises a first binding domain characterized by the presence of three light chain CDRs (i.e. CDR1, CDR2 and CDR3 of the VL region) and three heavy chain CDRs (i.e. CDR1, CDR2 and CDR3 of the VH region). The second binding domain preferably also comprises the minimum structural requirements of an antibody which allow for the target binding. More preferably, the second binding domain comprises at least three light chain CDRs (i.e. CDR1, CDR2 and CDR3 of the VL region) and/or three heavy chain CDRs (i.e. CDR1, CDR2 and CDR3 of the VH region). It is envisaged that the first and/or second binding domain is produced by or obtainable by phage-display or library screening methods rather than by grafting CDR sequences from a pre-existing (monoclonal) antibody into a scaffold. A binding domain may typically comprise an antibody light chain variable region (VL) and an antibody heavy chain variable region (VH); however, it does not have to comprise both. Fd fragments, for example, have two VH regions and often retain some antigen-binding function of the intact antigen-binding domain. Examples of (modified) antigen-binding antibody fragments include (1) a Fab fragment, a monovalent fragment having the VL, VH, CL and CH1 domains; (2) a F(ab')2 fragment, a bivalent fragment having two Fab fragments linked by a disulfide bridge at the hinge region; (3) an Fd fragment having the two VH and CH1 domains; (4) an Fv fragment having the VL and VH domains of a single arm of an antibody, (5) a dAb fragment (Ward et al., (1989) Nature 341:544-546), which has a VH domain; (6) an isolated complementarity determining region (CDR), and (7) a single chain Fv (scFv), the latter being preferred (for example, derived from an scFV-library).

In exemplary aspects, the therapeutic protein is a bi-specific antibody, a tri-specific antibody, a molecule, or an Fc fusion protein. In some aspects, the therapeutic protein comprises a single chain Fragment variable (scFv) which binds to a first target, optionally, wherein the therapeutic protein comprises a second scFV which binds to a second target (optionally different from the first target).

In some aspects, the therapeutic protein is a recombinant therapeutic protein, or an active fragment thereof. In other aspects, the therapeutic protein is endogenous to a cell or organisms and is isolated from the cell or organism.

ASPECTS OF THE PRESENT DISCLOSURE

The following aspects of the disclosure are exemplary only and not intended to limit the scope of the disclosure.

1. An ultraviolet (UV) based imaging system configured to determine protein concentrations of unknown protein samples based on automated multi-wavelength calibration, the UV based imaging system comprising: a light source configured to project a multi-wavelength light beam; a monochromator configured to receive the multi-wavelength light beam and to project, based on the multi-wavelength light beam, a range of single-wavelength light beams of a UV spectra; a sample holder operable for receiving a protein sample, the protein sample being either of (1) a standard protein sample selected from a set of standard protein samples, or (2) an unknown protein sample selected from a set of unknown protein samples, the unknown protein sample having an unknown protein concentration, wherein the sample holder is positioned to allow the range of single-wavelength light beams to pass through at least a portion of the protein sample; a detector operable to detect the range of single-wavelength light beams passing through the at least the portion of the protein sample; a memory storing program instructions; and a processor communicatively coupled to the memory, wherein the processor is configured to execute the program instructions to cause the processor to: receive a standard set of wavelength data as recorded by the detector for each standard protein sample of the set of standard protein samples, wherein the standard set of wavelength data includes, for each standard protein sample, a first series of first absorbance-to-wavelength value pairs across a first range of wavelengths selected from the range of the single-wavelength light beams, each first absorbance-to-wavelength value pair comprising a UV absorbance value and a wavelength value, generate a multi-wavelength calibration model based on each of the first series of first absorbance-to-wavelength value pairs of the standard set of wavelength data, receive an unknown set of wavelength data as recorded by the detector for each unknown protein sample of the set of unknown protein samples, wherein the unknown set of wavelength data includes, for each unknown protein sample, a second series of second absorbance-to-wavelength value pairs across a second range of wavelengths selected from the range of the single-wavelength light beams, each second absorbance-to-wavelength value pair comprising a UV absorbance value and a wavelength value, and determine with the multi-wavelength calibration model, for each unknown protein sample of the set of unknown protein samples, a plurality of protein concentration values, each protein concentration value of the plurality of protein concentration values corresponding to the second range of wavelengths selected from the range of the single-wavelength light beams.

2. The UV based imaging system of aspect 1, wherein the light source, the monochromator, the sample holder, and the detector comprise a portion of a spectrophotometer device.

3. The UV based imaging system of any of the aforementioned aspects, wherein the processor is communicatively coupled to the detector.

4. The UV based imaging system of any of the aforementioned aspects, wherein the memory or the processor is remote to the detector.

5. The UV based imaging system of any of the aforementioned aspects, wherein the set of standard protein samples comprises a plurality of standard protein samples, and wherein the set of unknown protein samples comprises a single protein sample having the unknown protein concentration.

6. The UV based imaging system of any of the aforementioned aspects, wherein the set of standard protein samples are protein standard solutions in the range of 0.1 to 220 milligrams (mg) per milliliter (ml).

7. The UV based imaging system of any of the aforementioned aspects, wherein the range of single-wavelength light beams comprises single-wavelength light beams in the UV spectra from 200 nanometers (nm) to 400 nanometers (nm).

8. The UV based imaging system of aspect 7, wherein each single-wavelength light beam in the UV spectra is separated by a one nanometer interval.

9. The UV based imaging system of any of the aforementioned aspects, wherein generating the multi-wavelength calibration model includes generating a single-wavelength calibration model for each of the first range of wavelengths selected from the range of the single-wavelength light beams, each single-wavelength calibration model comprising a slope value and a y-intercept value corresponding to UV absorbance of particular single wavelength.

10. The UV based imaging system of any of the aforementioned aspects, wherein the multi-wavelength calibration model is trained as a machine-learning model.

11. The UV based imaging system of any of the aforementioned aspects further comprising a standard wavelength data filter, the processor further configured to execute the program instructions to cause the processor to implement the standard wavelength data filter against the range of the single-wavelength light beams to select the first range of wavelengths.

12. The UV based imaging system of aspect 12, wherein the processor is further configured to execute the program instructions to cause the processor to implement the standard wavelength data filter to limit each first series of first absorbance-to-wavelength value pair based on UV absorbance values within a first filter range of UV absorbance values.

13. The UV based imaging system of any of the aforementioned aspects further comprising an unknown wavelength data filter, the processor further configured to execute the program instructions to cause the processor to implement the unknown wavelength data filter against the range of the single-wavelength light beams to select the second range of wavelengths.

14. The UV based imaging system of aspect 13, wherein the processor is configured to execute the program instructions to cause the processor to implement the unknown wavelength data filter to limit each second series of second absorbance-to-wavelength value pair based on UV absorbance values within a second filter range of UV absorbance values.

15. The UV based imaging system of any of the aforementioned aspects, wherein the processor is further configured to generate an enhanced prediction based on the plurality of protein concentration values.

16. The UV based imaging system of aspect 15, wherein the generating of the enhanced prediction comprises averaging each protein concentration value of the plurality of protein concentration values corresponding to the second range of wavelengths.

17. The UV based imaging system of any of the aforementioned aspects, wherein the multi-wavelength calibration model is used to monitor or measure protein concentration of a protein-related product.

18. The UV based imaging system of any of aspect 17, wherein the protein concentration is monitored or measured during manufacture of the protein-related product during manufacture of the protein-related product.

19. The UV based imaging system of any one or more of aspects 17 or 18, wherein the protein concentration of the protein-related product is compared against known specifications for the protein-related product.

20. The UV based imaging system of any one or more of aspects 17 to 19, wherein the protein-related product is a therapeutic product.

21. The UV based imaging system of any one or more of aspects 17 to 20, wherein the multi-wavelength calibration model inputs the second series of second absorbance-to-wavelength value pairs to predict each plurality of protein concentration values.

22. An ultraviolet (UV) based imaging method for determining protein concentrations of unknown protein samples based on automated multi-wavelength calibration, the UV based imaging method comprising: receiving, at a processor, a standard set of wavelength data as recorded by a detector for each standard protein sample of a set of standard protein samples, wherein the standard set of wavelength data includes, for each standard protein sample, a first series of first absorbance-to-wavelength value pairs across a first range of wavelengths selected from a range of a single-wavelength light beams of a UV spectra, each first absorbance-to-wavelength value pair comprising a UV absorbance value and a wavelength value; generating, with the processor, a multi-wavelength calibration model based on each of the first series of first absorbance-to-wavelength value pairs of the standard set of wavelength data; receiving, at the processor, an unknown set of wavelength data as recorded by the detector for each unknown protein sample of a set of unknown protein samples, wherein the unknown set of wavelength data includes, for each unknown protein sample, a second series of second absorbance-to-wavelength value pairs across a second range of wavelengths selected from the range of the single-wavelength light beams, each second absorbance-to-wavelength value pair comprising a UV absorbance value and a wavelength value; and determining, with the multi-wavelength calibration model as implemented on the processor, for each unknown protein sample of the set of unknown protein samples, a plurality of protein concentration values, each protein concentration value of the plurality of protein concentration values corresponding to the second range of wavelengths selected from the range of the single-wavelength light beams.

23. The UV based imaging method of aspect 22, wherein the detector comprises a portion of a spectrophotometer device.

24. The UV based imaging method of any one or more of aspects 22 to 23, wherein the processor is communicatively coupled to the detector.

25. The UV based imaging method of any one or more of aspects 22 to 24, wherein the processor is remote to the detector.

26. The UV based imaging method of any one or more of aspects 22 to 25, wherein the set of standard protein samples comprises a plurality of standard protein samples, and wherein the set of unknown protein samples comprises a single protein sample having the unknown protein concentration.

27. The UV based imaging method of any one or more of aspects 22 to 26, wherein the set of standard protein samples are protein standard solutions in the range of 0.1 to 220 milligrams (mg) per milliliter (ml).

28. The UV based imaging method of any one or more of aspects 22 to 27, wherein the range of single-wavelength light beams comprises single-wavelength light beams in the UV spectra from 200 nanometers (nm) to 400 nanometers (nm).

29. The UV based imaging method of aspect 28, wherein each single-wavelength light beam in the UV spectra is separated by a one nanometer interval.

30. The UV based imaging method of any one or more of aspects 22 to 28, wherein generating the multi-wavelength calibration model includes generating a single-wavelength calibration model for each of the first range of wavelengths selected from the range of the single-wavelength light beams, each single-wavelength calibration model comprising a slope value and a y-intercept value corresponding to UV absorbance of particular single wavelength.

31. The UV based imaging method of any one or more of aspects 22 to 30, wherein the multi-wavelength calibration model is trained as a machine-learning model.

32. The UV based imaging method of any one or more of aspects 22 to 31 further comprising a standard wavelength data filter, the processor further configured to execute the program instructions to cause the processor to implement the standard wavelength data filter against the range of the single-wavelength light beams to select the first range of wavelengths.

33. The UV based imaging method of aspect 32, wherein the processor is further configured to execute the program instructions to cause the processor to implement the standard wavelength data filter to limit each first series of first absorbance-to-wavelength value pair based on UV absorbance values within a first filter range of UV absorbance values.

34. The UV based imaging method of any one or more of aspects 22 to 33 further comprising an unknown wavelength data filter, the processor further configured to execute the program instructions to cause the processor to implement the unknown wavelength data filter against the range of the single-wavelength light beams to select the second range of wavelengths.

35. The UV based imaging method of aspect 34, wherein the processor is configured to execute the program instructions to cause the processor to implement the unknown wavelength data filter to limit each second series of second absorbance-to-wavelength value pair based on UV absorbance values within a second filter range of UV absorbance values.

36. The UV based imaging method of any one or more of aspects 22 to 35, wherein the processor is further configured to generate an enhanced prediction based on the plurality of protein concentration values.

37. The UV based imaging method of aspect 36, wherein the generating of the enhanced prediction comprises averaging each protein concentration value of the plurality of protein concentration values corresponding to the second range of wavelengths.

38. The UV based imaging method of any one or more of aspects 22 to 37, wherein the multi-wavelength calibration model is used to monitor or measure protein concentration of a protein-related product.

39. The UV based imaging method of aspect 38, wherein the protein concentration is monitored or measured during manufacture of the protein-related product.

40. The UV based imaging method of aspect 38 or 39, wherein the protein concentration of the protein-related product is compared against known specifications for the protein-related product.

41. The UV based imaging system of any one or more of aspects 38 to 40, wherein the protein-related product is a therapeutic product.

42. The UV based imaging method of any one or more of aspects 22 to 41, wherein the multi-wavelength calibration model inputs the second series of second absorbance-to-wavelength value pairs to predict each plurality of protein concentration values.

43. A tangible, non-transitory computer-readable medium storing instructions for determining protein concentrations of unknown protein samples based on automated multi-wavelength calibration, that when executed by one or more processors of a computing device, cause the computing device to: receive, at a processor, a standard set of wavelength data as recorded by a detector for each standard protein sample of a set of standard protein samples, wherein the standard set of wavelength data includes, for each standard protein sample, a first series of first absorbance-to-wavelength value pairs across a first range of wavelengths selected from a range of a single-wavelength light beams of a UV spectra, each first absorbance-to-wavelength value pair comprising a UV absorbance value and a wavelength value; generate, with the processor, a multi-wavelength calibration model based on each of the first series of first absorbance-to-wavelength value pairs of the standard set of wavelength data; receive, at the processor, an unknown set of wavelength data as recorded by the detector for each unknown protein sample of a set of unknown protein samples, wherein the unknown set of wavelength data includes, for each unknown protein sample, a second series of second absorbance-to-wavelength value pairs across a second range of wavelengths selected from the range of the single-wavelength light beams, each second absorbance-to-wavelength value pair comprising a UV absorbance value and a wavelength value; and determine, with the multi-wavelength calibration model as implemented on the processor, for each unknown protein sample of the set of unknown protein samples, a plurality of protein concentration values, each protein concentration value of the plurality of protein concentration values corresponding to the second range of wavelengths selected from the range of the single-wavelength light beams.

44. An imaging apparatus for determining protein concentrations of unknown protein samples based on automated multi-wavelength calibration, the imaging apparatus comprising: a means for receiving a standard set of wavelength data for each standard protein sample of a set of standard protein samples, wherein the standard set of wavelength data includes, for each standard protein sample, a first series of first absorbance-to-wavelength value pairs across a first range of wavelengths selected from a range of a single-wavelength light beams of a UV spectra, each first absorbance-to-wavelength value pair comprising a UV absorbance value and a wavelength value; a means for generating a multi-wavelength calibration model based on each of the first series of first absorbance-to-wavelength value pairs of the standard set of wavelength data; a means for receiving an unknown set of wavelength data for each unknown protein sample of a set of unknown protein samples, wherein the unknown set of wavelength data includes, for each unknown protein sample, a second series of second absorbance-to-wavelength value pairs across a second range of wavelengths selected from the range of the single-wavelength light beams, each second absorbance-to-wavelength value pair comprising a UV absorbance value and a wavelength value; and a means for determining, with the multi-wavelength calibration model, for each unknown protein sample of the set of unknown protein samples, a plurality of protein concentration values, each protein concentration value of the plurality of protein concentration values corresponding to the second range of wavelengths selected from the range of the single-wavelength light beams.

45. The UV based imaging method of any one or more of aspects 22 to 41, wherein at least one unknown protein sample of the set of unknown protein samples comprises a protein therapeutic.

46. The UV based imaging method of aspect 45, wherein the protein therapeutic is selected from the group consisting of an antibody, an antigen-binding antibody fragment, an antibody protein product, a Bi-specific T cell engager (BiTE®) molecule, a bispecific antibody, a trispecific antibody, an Fc fusion protein, a recombinant protein, and an active fragment of a recombinant protein.

ADDITIONAL CONSIDERATIONS

Although the disclosure herein sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location, while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other embodiments, the one or more processors or processor-implemented modules may be distributed across a number of geographic locations.

This detailed description is to be construed as exemplary only and does not describe every possible embodiment, as describing every possible embodiment would be impractical, if not impossible. A person of ordinary skill in the art may implement numerous alternate embodiments, using either current technology or technology developed after the filing date of this application.

Those of ordinary skill in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

The invention claimed is:

1. An ultraviolet (UV) based imaging system configured to determine protein concentrations of unknown protein samples based on automated multi-wavelength calibration, the UV based imaging system comprising:
    a light source configured to project a multi-wavelength light beam;
    a monochromator configured to receive the multi-wavelength light beam and to project, based on the multi-wavelength light beam, a range of single-wavelength light beams of a UV spectra;
    a sample holder structure positioned for receiving a protein sample, the protein sample being either of (1) a standard protein sample selected from a set of standard protein samples, or (2) an unknown protein sample selected from a set of unknown protein samples, the unknown protein sample having an unknown protein concentration, wherein the sample holder is positioned to allow the range of single-wavelength light beams to pass through at least a portion of the protein sample;
    a light-sensitive detector device configured to detect the range of single-wavelength light beams passing through the at least the portion of the protein sample, wherein the light-sensitive detector device is configured to determine absorbance values by measuring a variance between the projected range of single-wavelength light beams by the monochromator and the single-wavelength light beams passed through the at least the portion of the protein sample;
    a memory storing program instructions and configured to store as wavelength data the range of single-wavelength light beams that pass through the at least the portion of the standard sample and the at least the portion of the unknown sample; and
    a processor communicatively coupled to the memory, wherein the processor is configured to execute the program instructions to cause the processor to:
    receive, from the memory, a standard set of wavelength data as recorded by the detector for each standard protein sample of the set of standard protein samples, wherein the standard set of wavelength data includes, for each standard protein sample, a first series of first absorbance-to-wavelength value pairs across a first range of wavelengths selected from the range of the single-wavelength light beams, each first absorbance-to-wavelength value pair comprising a UV absorbance value and a wavelength value,
    generate a multi-wavelength calibration model based on each of the first series of first absorbance-to-wavelength value pairs of the standard set of wavelength data,
    receive, from the memory, an unknown set of wavelength data as recorded by the detector for each unknown protein sample of the set of unknown protein samples, wherein the unknown set of wavelength data includes, for each unknown protein sample, a second series of second absorbance-to-wavelength value pairs across a second range of wavelengths selected from the range of the single-wavelength light beams, each second absorbance-to-wavelength value pair comprising a UV absorbance value and a wavelength value, and
    determine with the multi-wavelength calibration model, for each unknown protein sample of the set of unknown protein samples, a plurality of protein concentration values, each protein concentration value of the plurality of protein concentration values corresponding to the second range of wavelengths selected from the range of the single-wavelength light beams.

2. The UV based imaging system of claim 1, wherein the light source, the monochromator, the sample holder, and the detector form a portion of a spectrophotometer device.

3. The UV based imaging system of claim 1, wherein the processor is communicatively coupled to the detector.

4. The UV based imaging system of claim 1, wherein the memory or the processor is remote to the detector.

5. The UV based imaging system of claim 1, wherein the set of standard protein samples comprises a plurality of standard protein samples, and wherein the set of unknown protein samples comprises a single protein sample having the unknown protein concentration.

6. The UV based imaging system of claim 1, wherein the set of standard protein samples are protein standard solutions in the range of 0.1 to 220 milligrams (mg) per milliliter (ml).

7. The UV based imaging system of claim 1, wherein the range of single-wavelength light beams comprises single-wavelength light beams in the UV spectra from 200 nanometers (nm) to 400 nanometers (nm).

8. The UV based imaging system of claim 1, wherein generating the multi-wavelength calibration model includes generating a single-wavelength calibration model for each of the first range of wavelengths selected from the range of the single-wavelength light beams, each single-wavelength calibration model comprising a slope value and a y-intercept value corresponding to UV absorbance of particular single wavelength.

9. The UV based imaging system of claim 1, wherein the multi-wavelength calibration model is trained as a machine-learning model.

10. The UV based imaging system of claim 1, further comprising a standard wavelength data filter, the processor further configured to execute the program instructions to cause the processor to implement the standard wavelength data filter against the range of the single-wavelength light beams to select the first range of wavelengths.

11. The UV based imaging system of claim 1, further comprising an unknown wavelength data filter, the processor further configured to execute the program instructions to cause the processor to implement the unknown wavelength data filter against the range of the single-wavelength light beams to select the second range of wavelengths.

12. The UV based imaging system of claim 7, wherein each single-wavelength light beam in the UV spectra is separated by a one nanometer interval.

13. The UV based imaging system of claim 10, wherein the processor is further configured to execute the program instructions to cause the processor to implement the standard wavelength data filter to limit each first series of first absorbance-to-wavelength value pair based on UV absorbance values within a first filter range of UV absorbance values.

14. The UV based imaging system of claim 11, wherein the processor is configured to execute the program instructions to cause the processor to implement the unknown wavelength data filter to limit each second series of second absorbance-to-wavelength value pair based on UV absorbance values within a second filter range of UV absorbance values.

15. An ultraviolet (UV) based imaging method for determining protein concentrations of unknown protein samples based on automated multi-wavelength calibration, the UV based imaging method comprising:
projecting a multi-wavelength light beam toward a monochromator;
projecting a range of single-wavelength light beams based on the multi-wavelength light beam toward a protein sample, wherein the protein sample includes either an unknown protein sample or a standard protein sample;
detecting a range of single-wavelength light beams that pass through at least a portion of the protein sample;
recording the range of single-wavelength light beams as wavelength data;
receiving, at a processor, a standard set of wavelength data as recorded by a detector for each standard protein sample of a set of standard protein samples, wherein the standard set of wavelength data includes, for each standard protein sample, a first series of first absorbance-to-wavelength value pairs across a first range of wavelengths selected from a range of a single-wavelength light beams of a UV spectra, each first absorbance-to-wavelength value pair comprising a UV absorbance value and a wavelength value;
generating, with the processor, a multi-wavelength calibration model based on each of the first series of first absorbance-to-wavelength value pairs of the standard set of wavelength data;
receiving, at the processor, an unknown set of wavelength data as recorded by the detector for each unknown protein sample of a set of unknown protein samples, wherein the unknown set of wavelength data includes, for each unknown protein sample, a second series of second absorbance-to-wavelength value pairs across a second range of wavelengths selected from the range of the single-wavelength light beams, each second absorbance-to-wavelength value pair comprising a UV absorbance value and a wavelength value; and
determining, with the multi-wavelength calibration model as implemented on the processor, for each unknown protein sample of the set of unknown protein samples, a plurality of protein concentration values, each protein concentration value of the plurality of protein concentration values corresponding to the second range of wavelengths selected from the range of the single-wavelength light beams.

16. The UV based imaging method of claim 15, wherein the processor is further configured to generate an enhanced prediction based on the plurality of protein concentration values.

17. The UV based imaging method of claim 15, wherein at least one unknown protein sample of the set of unknown protein samples comprises a protein therapeutic.

18. The UV based imaging method of claim 16, wherein the generating of the enhanced prediction comprises averaging each protein concentration value of the plurality of protein concentration values corresponding to the second range of wavelengths.

19. The UV based imaging method of claim 17, wherein the protein therapeutic is selected from the group consisting of an antibody, an antigen-binding antibody fragment, an antibody protein product, a Bi-specific T cell engager molecule, a bispecific antibody, a trispecific antibody, an Fc fusion protein, a recombinant protein, and an active fragment of a recombinant protein.

20. A tangible, non-transitory computer-readable medium storing instructions for determining protein concentrations of unknown protein samples based on automated multi-wavelength calibration, that when executed by one or more processors of a computing device, cause the computing device to:
receive, at a processor, a standard set of wavelength data as recorded by a detector for each standard protein sample of a set of standard protein samples, wherein the standard set of wavelength data includes, for each standard protein sample, a first series of first absorbance-to-wavelength value pairs across a first range of wavelengths selected from a range of a single-wavelength light beams of a UV spectra, each first absorbance-to-wavelength value pair comprising a UV absorbance value and a wavelength value;
generate, with the processor, a multi-wavelength calibration model based on each of the first series of first absorbance-to-wavelength value pairs of the standard set of wavelength data;
receive, at the processor, an unknown set of wavelength data as recorded by the detector for each unknown protein sample of a set of unknown protein samples, wherein the unknown set of wavelength data includes, for each unknown protein sample, a second series of second absorbance-to-wavelength value pairs across a second range of wavelengths selected from the range of the single-wavelength light beams, each second absorbance-to-wavelength value pair comprising a UV absorbance value and a wavelength value; and determine, with the multi-wavelength calibration model as implemented on the processor, for each unknown protein sample of the set of unknown protein samples, a plurality of protein concentration values, each protein concentration value of the plurality of protein concentration values corresponding to the second range of wavelengths selected from the range of the single-wavelength light beams.

\* \* \* \* \*